(12) United States Patent
Toreki et al.

(10) Patent No.: US 8,545,862 B2
(45) Date of Patent: Oct. 1, 2013

(54) POLYELECTROLYTE COMPLEX FOR IMPARTING ANTIMICROBIAL PROPERTIES TO A SUBSTRATE

(75) Inventors: William Toreki, Gainesville, FL (US); David N. Moore, Gainesville, FL (US); Bernd Liesenfeld, Gainesville, FL (US); Albina Mikhaylova, Gainesville, FL (US); Gerald M. Olderman, Bedford, MA (US)

(73) Assignee: Quick-Med Technologies, Inc., Gainesville, FL (US)

( * ) Notice: Subject to any disclaimer, the term of this patent is extended or adjusted under 35 U.S.C. 154(b) by 0 days.

(21) Appl. No.: 12/830,062

(22) Filed: Jul. 2, 2010

(65) Prior Publication Data

US 2010/0291169 A1 Nov. 18, 2010

Related U.S. Application Data

(63) Continuation of application No. PCT/US2009/051163, filed on Jul. 20, 2009.

(60) Provisional application No. 61/082,076, filed on Jul. 18, 2008.

(51) Int. Cl.
*A01N 25/00* (2006.01)

(52) U.S. Cl.
USPC ...................................................... 424/405

(58) Field of Classification Search
USPC .................................... 514/255; 424/405
See application file for complete search history.

(56) References Cited

U.S. PATENT DOCUMENTS

| 4,504,541 A | 3/1985 | Yasuda et al. |
| 5,578,598 A | 11/1996 | Abe et al. |
| 5,658,915 A | 8/1997 | Abe et al. |
| 6,060,410 A | 5/2000 | Gillberg-LaForce et al. |
| 6,558,622 B1 | 5/2003 | Malchesky |
| 6,936,746 B2 | 8/2005 | Effing et al. |
| 7,205,369 B2 | 4/2007 | Song |
| 7,238,752 B2 | 7/2007 | Song |
| 2004/0034156 A1 | 2/2004 | Song |
| 2004/0167459 A1 | 8/2004 | Higuchi et al. |
| 2005/0261419 A1 | 11/2005 | Song |
| 2006/0021150 A1 | 2/2006 | Hu et al. |
| 2006/0183822 A1 | 8/2006 | Nguyen-Kim et al. |
| 2006/0204533 A1 | 9/2006 | Hsu et al. |
| 2007/0154513 A1 | 7/2007 | Atanasoska et al. |
| 2007/0243237 A1 | 10/2007 | Khaled et al. |
| 2008/0005852 A1 | 1/2008 | Hu et al. |
| 2008/0206293 A1* | 8/2008 | Toreki et al. ................ 424/404 |

FOREIGN PATENT DOCUMENTS

| WO | WO2006/015080 | 2/2006 |
| WO | WO2006099514 | 9/2006 |
| WO | WO2007024972 | 3/2007 |
| WO | WO2007078516 | 7/2007 |
| WO | WO2008027989 | 3/2008 |

* cited by examiner

*Primary Examiner* — Benjamin Packard
(74) *Attorney, Agent, or Firm* — Gerry J. Elman; Elman Technology Law, P.C.

(57) ABSTRACT

Anionic polyelectrolytes are used as binding agents to reduce the solubility of cationic antimicrobial polyelectrolytes. Ionic attraction between the anionic stabilizing polyelectrolytes and the antimicrobial cationic polyelectrolytes results in formation of a polyelectrolyte complex (PEC). A treatment liquid comprising a stable colloid, suspension, dispersion, solution, coacervate, or emulsion of the PEC in an aqueous carrier is used to treat an article, thus coating, infiltrating, or infusing the PEC onto or into the article. Subsequent drying results in an antimicrobial article wherein the PEC is bound to the article and is significantly less prone, relative to either of the component polyelectrolytes, to being washed, leached, leaked, extracted, or migrated from the antimicrobial article during use, or when exposed to aqueous fluids or solvents. The antimicrobial article can be further treated with ethylene oxide which enhances its antimicrobial efficacy, its biocompatibility, and its utility in wound dressings, medical devices, clothing, etc.

41 Claims, No Drawings

POLYELECTROLYTE COMPLEX FOR IMPARTING ANTIMICROBIAL PROPERTIES TO A SUBSTRATE

CROSS-REFERENCE TO RELATED APPLICATIONS

This application is a continuation of our International Patent Application, Serial Number PCT/US2009/051163, filed Jul. 20, 2009, which claims benefit of U.S. Provisional Patent Application 61/082,076 filed Jul. 18, 2008. This application claims priority to both prior applications. The entire disclosures of each of the aforementioned applications are incorporated herein by reference.

TECHNICAL FIELD

The present invention relates to the preparation of antimicrobial materials, by affixing antimicrobial polymers to the surface of a substrate or article, such as a wound dressing, medical device, or textile.

BACKGROUND ART

Polyelectrolyte complexes (PEC) are known in the literature and have been used for a variety of purposes including surface antimicrobial activity, surface antistatic activity, controlled release drug delivery, dampening devices, paper coatings, and personal care products.

The following patents are cited as background information for this application.
U.S. Patents or Patent Applications:
U.S. Pat. No. 4,504,541 to Yasuda et al. Issued Mar. 12, 1985.
U.S. Pat. No. 5,678,915 to Abe. Issued Aug. 19, 1997
U.S. Pat. No. 6,060,410 to Gillberg-LaForce et al. Issued May 9, 2000.
U.S. App. 2004/0034156 to Song. Published Feb. 19. 2004.
U.S. App. 2005/0261419 to Song. Published Jul. 27, 2005.
U.S. Pat. No. 6,936,746 to Effing et al. Issued Aug. 30, 2005.
U.S. App. 2006/0021150 to Hu et al. Published Feb. 2, 2006.
U.S. App 2006/0183822 to Nguyen-Kim et al. Published Aug. 17, 2006.
U.S. App. 2006/0204533 to Hsu et al. Published Sep. 14, 2006.
U.S. Pat. No. 7,205,369 to Song. Issued Apr. 17, 2007.
U.S. Pat. No. 7,238,752 to Song. Issued Jul. 3, 2007.
U.S. App. 2007/0154513 to Atanasoska et al. Published Jul. 5, 2007.
U.S. App. 2007/0243237 to Khaled et al. Published Oct. 18, 2007.
U.S. App. 2008/0005852 to Hu et al. Published Jan. 10, 2008.
Foreign Patents or Patent Applications:
WIPO PCT Publication 06/015080 to Nanotex, LLC. Published Feb. 9, 2006.
WIPO PCT Publication 06/099514 to Biotegra, Inc. Published Sep. 21, 2006.
WIPO PCT Publication 07/024972 to Quick-Med Technologies, Inc. and University of Florida Research Foundation, Inc. Published Mar. 1, 2007.
WIPO PCT Publication 07/078516 to Boston Scientific Scimed, Inc. Published Jul. 12, 2007.
WIPO PCT Publication 08/027989 to Florida State University Research Foundation, Inc. Published Mar. 6, 2008.

SUMMARY OF THE INVENTION

The present invention relates to using anionic stabilizing polymers as binding agents to reduce the solubility of cationic antimicrobial polymers. Ionic attraction between the polymers results in the formation of a polyelectrolyte complex (PEC). Low levels, less than 1%, of the resulting PEC can be used to impart antimicrobial properties to substrates such as wound dressings, medical devices, textiles, clothing, personal care products, and other materials which would benefit from antimicrobial protection.

This invention pertains to using anionic polyelectrolytes as binding agents to reduce the solubility of cationic antimicrobial polyelectrolytes. Ionic attraction between the oppositely-charged anionic stabilizing polyelectrolytes and antimicrobial cationic polyelectrolytes results in formation of a polyelectrolyte complex (PEC). A treatment liquid comprising a stable colloid, suspension, dispersion, solution, coacervate, or emulsion of the PEC in an aqueous carrier is used to treat an absorbent substrate, thus coating, infiltrating, or infusing the PEC onto or into the substrate. Subsequent drying results in an antimicrobial article which is coated/infused with the PEC. The PEC is thus bound to the substrate and is significantly less prone, than either of the component polyelectrolytes would be in the absence of the other, to being washed-off (out), leached, leaked, extracted, or migrated from the substrate during use, or when exposed to aqueous fluids or solvents. The antimicrobial article prepared in this manner exhibits antimicrobial properties, is biocompatible, and may be utilized in wound dressings, medical devices, clothing, etc.

One embodiment of this invention is to provide a method for forming an antimicrobial article that has an antimicrobial polyelectrolyte complex bound to it. These materials are useful as antimicrobial wound dressings, medical devices, clothing, etc.

One embodiment of this invention is to provide an antimicrobial article that has an antimicrobial cationic polyelectrolyte bound to it, wherein said antimicrobial article exhibits non-leachable antimicrobial properties and is biocompatible. These materials are useful as antimicrobial wound dressings, medical devices, clothing, etc, or as components thereof.

An embodiment of this invention is to provide a method of manufacturing a treated substrate wherein said method of manufacture includes conducting assays, tests, or measurements to verify, validate, demonstrate, or confirm that the treated substrate exhibits non-leaching antimicrobial properties, and/or is biocompatible. The assays, tests, or measurements may comprise testing for antimicrobial efficacy of the treated substrate, or testing for the presence of antimicrobial cationic polyelectrolyte remaining bound to the treated substrate after the treated substrate has been exposed to actual or simulated use conditions such as extraction or exposure to fluids. Alternatively, the assays, tests, or measurements may comprise testing of an extract, rinsate, leachate, or other fluid which has been in contact with the treated substrate, to show a lack of antimicrobial activity therein, or an absence of appreciable antimicrobial cationic polyelectrolyte therein. The assays, tests, or measurements may comprise in-vivo or in-vitro biocompatibility assays such as cytotoxicity, irritation, sensitization, and the like.

Another embodiment of this invention is to provide a method of preparing an antimicrobial article which comprises treating a substrate with a treatment liquid comprising a stable colloid, suspension, dispersion, solution, coacervate, or emulsion of a PEC in an aqueous medium, wherein said PEC is formed by mixing or combining an aqueous solution of an anionic polyelectrolyte with a stoichiometric excess of an aqueous solution of a cationic polyelectrolyte, followed by drying of the treated substrate, wherein the ratio of cationic polyelectrolyte relative to anionic polyelectrolyte is sufficient to impart antimicrobial properties to the substrate, and wherein the PEC is non-leachably bound to the substrate and is less prone, than either of the component polyelectrolytes would be in the absence of the other, to being washed-off (out), leached, leaked, extracted, or migrated from the substrate during use, or when exposed to aqueous fluids or solvents.

It is an embodiment of this invention that the overall amount of the cationic polyelectrolyte in the treatment liquid comprising a stable colloid, suspension, dispersion, solution, coacervate, or emulsion of the PEC in an aqueous carrier and in the finished treated material is controlled, or optimized so as to maximize the antimicrobial efficacy of the material, while minimizing undesirable effects or properties. For instance, too high a content of cationic polyelectrolyte could cause toxicity due to a higher concentration of extractable cationic polyelectrolyte, or adversely affect the physical or aesthetic properties of the antimicrobial article.

A preferred embodiment of this invention is a antimicrobial article comprising a substrate, a cationic polyelectrolyte, and an anionic polyelectrolyte, wherein the cationic polyelectrolyte, being present in a molar excess relative to anionic polyelectrolyte, imparts antimicrobial properties to the material, and wherein complexation between the anionic and cationic polyelectrolytes makes the cationic polyelectrolyte less prone, than either of the component polyelectrolytes would be in the absence of the other, to being washed-off (out), leached, leaked, extracted, or migrated from the substrate during use, or when exposed to aqueous fluids or solvents.

In a preferred embodiment of this invention the cationic polyelectrolyte is a quaternary ammonium polymer or a quaternary ammonium copolymer. In a more preferred embodiment, the cationic polyelectrolyte is poly(diallyldimethylammonium chloride), also known as polyDADMAC.

Another embodiment of the inventive method is to use any temperature and time combination that results in drying of said material. As used herein, dried means, for instance, that an article exposed to a solution of antimicrobial cationic polyelectrolytes is then dried to a constant weight.

It is an aspect of the current inventive method that it can establish a non-leaching attachment of antimicrobial cationic polyelectrolytes or antimicrobial polyelectrolyte complexes to a variety of substrates.

The preferred embodiments of the present invention include a method for preparing the polyelectrolyte complex, method for preparing the antimicrobial article or substrate, that comprises all or part of a wound dressing, a burn dressing, a bandage, a sanitary pad, a tampon, an intrinsically or inherently antimicrobial absorbent dressing, a diaper, toilet paper, a sanitary wipe, a sponge, a cotton swab, a surgical gown, an isolation gown, a lab coat, a glove, surgical scrubs, a head cover, a hair cover, a face mask, an exam table cover, a cast liner, a splint liner, padding, gauze, sterile packaging, a mattress cover, bedding, a sheet, a towel, clothing, underwear, a sock, shoe-cover, a pressure sensitive adhesive, an automobile air filter, an airplane air filter, an HVAC system air filter, a military protective garment, an apparatus for protection against a biohazard or biological warfare agent, lumber, food packaging material, meat packaging material, fish packaging material, apparel for food handling, a surface for food preparation, carpet, wood, lumber, paper, or paper currency.

In a preferred embodiment of this invention, a substrate modified by attachment of an antimicrobial PEC or antimicrobial cationic polymer is subjected to treatment with ethylene oxide in order to enhance the antimicrobial power of the antimicrobial article.

Definitions

As used herein, the following terms have the following meanings.

"Antimicrobial" refers to the microbicidal or microbistatic properties of a compound, composition, article, or material that enables it to kill, destroy, inactivate, or neutralize a microbe microorganism; or to prevent or reduce the growth, ability to survive, or propagation of a microorganism. As used herein, "microbe" or "microorganism" refers to any organism or combination of organisms able to cause infection, such as bacteria, viruses, protozoa, yeasts, fungi, molds, or spores formed by any of these.

"Substrate" refers to a surface or medium upon, or in which an antimicrobial polyelectrolyte is bonded.

"Cationic polyelectrolyte" means a polymer molecule with multiple cationic sites or moieties which are covalently bonded to the polymer, or attached to the molecular structure of the antimicrobial polymer by covalent chemical bonds, and are part of the polymer molecular structure, and that said cationic sites or moieties are located either in the main-chain of the polymer, or in side-groups of the polymer.

"Anionic polyelectrolyte" means a polymer molecule with multiple anionic sites or moieties which are covalently bonded to the polymer, or attached to the molecular structure of the polymer by covalent chemical bonds, and are part of the polymer molecular structure, and that said cationic sites or moieties are located either in the main-chain of the polymer, or in side-groups of the polymer.

"Main-chain" and "side-groups" are terms commonly used to describe polymer molecular structure and will be familiar to one skilled in the art.

The term "quaternary ammonium" is common chemical nomenclature and its meaning will be understood by one skilled in the art. There are two types of ammonium compounds: acidic, and non-acidic. Acidic ammonium compounds are acid salts of amines, and are characterized by having an N—H covalent bond wherein the N—H bond is reactive with and may protonate bases. Non-acidic, or "quaternary" ammonium compounds do not have this N—H bond, and are not reactive with bases in the same way. Quaternary ammonium compounds are generally characterized by having four covalent bonds, usually four carbon-nitrogen bonds attached to the positively-charged central nitrogen. Quaternary ammonium polymers are also known as "polyquats" or "polyquaterniums". Non-acidic quaternary ammonium compounds are preferred in the practice of this invention.

By "inherently antimicrobial", or "intrinsically antimicrobial" is meant a property of a material wherein said material would exhibit antimicrobial activity or properties in the absence of any antimicrobial activity or properties contributed by agents, compounds, or additives which are not integral to the material, not chemically bonded to the material, or detachable from the material. "Inherently antimicrobial", or "intrinsically antimicrobial" materials exhibit antimicrobial activity even after the removal or depletion of such agents, compounds, or additives from the material. "Inherently antimicrobial", or "intrinsically antimicrobial" does not mean that the material contains no leachable agents with antimicrobial activity.

By "non-leachably bound" is meant that the antimicrobial cationic polyelectrolytes of the present invention, once attached to the material, substrate, or article via the method of the current invention, do not appreciably separate from, migrate out of, or away from the material, substrate, or article and enter a wound, or otherwise become non-integral with the material, substrate, or article under standard uses. By "not appreciably separate" is meant that no more than an insubstantial amount of antimicrobial cationic polyelectrolyte separates, for example less than one percent, preferably less than 0.1 percent, more preferably less than 0.01 percent, and even more preferably less than 0.001 percent of the total quantity of antimicrobial cationic polyelectrolyte. Alternatively, "not appreciably separate" means that the solution concentration of antimicrobial cationic polyelectrolyte resulting from separation of attached antimicrobial cationic polyelectrolyte from the treated substrate, in a liquid in contact with the material, substrate, or article when extracted by methods described herein, does not exceed a predetermined level, for example less than 200 ppm, preferably less than 100 ppm, and more preferably less than or equal to 60 ppm. Alternatively, depending on the application, "not appreciably separate" may mean that no adverse effect on wound healing or the health of an adjacent tissue of interest due to leaching of the antimicrobial cationic polyelectrolyte is measurable. It should be understood that particular definition may depend on the application in which the invention is used. For instance, in textile applications, the desire is to maintain efficacy over a prolonged period of use, thus only a very gradual loss of antimicrobial material over an extended time would be acceptable, regardless of the amount leached at any given point in time. For medical applications such as wound dressings, the overriding concern would be to ensure that the localized concentration of leachable material remains below a specific level at a given point in time, or leads to no adverse effects over the period of use. Alternatively, "non-leachably bound" means increased resistance to the immobilized PEC against being washed-off (out), leached, leaked, extracted, or migrated from the antimicrobial article during use, or when exposed to aqueous fluids or solvents, relative to the behavior of the cationic polyelectrolyte alone (i.e. in absence of the anionic component used to form the PEC).

By "substantially unleachable" is meant that, when the antimicrobial cationic polyelectrolytes of the present invention are attached to the material, substrate, or article via the method of the current invention, less than fifty (50) percent of the total quantity of antimicrobial cationic polyelectrolyte separates from, or migrates out of, or away from the material, substrate, or article, enter a wound, or otherwise become non-integral with the material, substrate, or article under standard conditions. Preferably, substantially unleachable means less than thirty (30) percent of the total quantity of antimicrobial polyelectrolyte separates or migrates away from the substrate. More preferably, less than fifteen (15) percent of the antimicrobial cationic polyelectrolyte separates or migrates from the substrate. Even more preferably, less than ten (10) percent separates or migrates from the substrate. Most preferably, less than five (5) percent of the antimicrobial cationic polyelectrolyte separates or migrates from the substrate.

In regard to the foregoing definition, it is noted that "non-leachably bound" refers to the bond between the PEC and the substrate or article. In certain embodiments of the present invention, a bond between the polymer backbone of the PEC and one or more type of antimicrobial group may be intentionally made to be more susceptible to release, and therefore more leachable. This may provide a benefit where it is desirable for a percentage of the antimicrobial groups to be selectively released under certain conditions. However, it is noted that the typical bond between the polymer chain and antimicrobial groups envisioned and enabled herein are covalent bonds that do not leach under standard exposure conditions.

By "biocompatible" is meant that the material is compatible with living cells, tissues, organs, or systems, and poses no risk of injury, toxicity, or rejection by the immune system, or that the material does not cause excessive irritation, cytotoxicity, or sensitization.

"No effect on the body" means that the material does not interfere with wound healing or normal bodily processes, and that it does not cause excessive injury, toxicity, irritation, cytotoxicity, sensitization, or rejection by the immune system.

By "degree of polymerization" is meant the number of monomers (molecular repeat units) that are joined in a single polymer chain. For example, in a preferred embodiment of the invention, the average degree of polymerization of the cationic polyelectrolyte is in the range of about 10 to 10,000. In another embodiment, the preferred average degree of polymerization is in the range of about 100 to 5,000, and in yet another embodiment, the preferred average degree of polymerization is in the range of about 1,000 to 3,000.

As used herein, the term "polyelectrolyte" denotes a class of macromolecular compounds which, when dissolved in a suitable solvent, such as water, spontaneously acquire or can be made to acquire a large number of elementary charges distributed along the macromolecular chain. When the polyelectrolyte spontaneously acquires its maximum number of charges, it is referred to herein as a "strong polyelectrolyte." When the polyelectrolyte is only partially charged when dissolved in a pure solvent, it is referred to herein as a "weak polyelectrolyte." Both weak and strong polyelectrolytes may have either anionic charges or cationic charges. The term is intended to encompass a single polyelectrolyte or a mixture of two or more polyelectrolytes of the same type (i.e., anionic or cationic polyelectrolytes).

It should be noted that the term "polyelectrolyte" also is intended to encompass a polyelectrolyte having both cationic and anionic groups, provided that one type of such groups is present in an amount sufficient to permit the formation of a nonstoichiometric polyelectrolyte complex as described herein; that is, one type of ionizable group must be predominant. Such a polyelectrolyte may be, by way of illustration, a block, graft, or random copolymer. For example, the ratio of the number of predominant ionizable groups to the number of ionizable groups having an opposite charge may be at least about 2. In addition, the term is intended to include a single polyelectrolyte having both types of ionizable groups, a mixture of two or more polyelectrolytes having the same type of predominant ionizable groups, and a mixture of two or more polyelectrolytes in which at least one polyelectrolyte contains both types of ionizable groups and at least one polyelectrolyte contains only one type of ionizable groups, provided the predominant ionizable groups and the one type of ionizable groups, respectively, are of the same type (i.e., either anionic or cationic). Although coming within the scope of the present invention, polyelectrolytes containing both types of groups are not desired as they may form internal or intramolecular complexes and/or interfere with complex formation with the other polyelectrolyte required by the present invention.

The term "latent charge" is used herein in reference to the charge which a polyelectrolyte exhibits in an aqueous solution. In the dry state, the ionizable groups are neutral; consequently, the polyelectrolyte per se does not have a charge. For this reason, the ionizable groups of the polyelectrolyte are referred to as having a "latent charge." A particular polyelectrolyte, when placed in an aqueous medium, typically, contains a number of ionized groups having the same charge. That is, such groups are either positive or negative. The term "opposite" in reference to such charge (the "latent charge" in the dry or nonhydrated state), simply means that if one of the first and second polyelectrolytes has a positive charge in solution (or a positive latent charge), the other must have a charge which is opposite, i.e., a negative charge (or a negative latent charge). Positively charged and negatively charged ionized groups sometimes are referred to herein as cationic groups and anionic groups, respectively, or variations thereof.

The terms "antimicrobial article", "modified article", "treated article", "treated material" "modified material", "treated substrate", and "modified substrate" are used interchangeably herein, and refer to an article or substrate material that has been exposed to the treatment liquid consisting essentially of a stable colloid, suspension, dispersion, solution, coacervate, or emulsion of the PEC according to the methods described herein.

"Stable", as used to describe a treatment liquid comprising a stable colloid, suspension, dispersion, solution, coacervate, or emulsion of the PEC in an aqueous carrier, means that significant or non-reversible phase separation, coagulation, or formation of solids, precipitates, flocs, agglomerates, or particles of the PEC does not occur during the normal storage or usage of the treatment liquid. "Phase separation" refers to macroscopic separation of the liquid into distinct layers and does not refer to the microscopic phase separation that is evidenced by a cloudy or milk-like appearance of the treatment liquid. In this context, "nonreversible" means that the desirable original state of the treatment liquid cannot be restored by simple mixing or stirring of the treatment liquid.

The term "aqueous medium" is used herein to mean any liquid medium which consists essentially of water. Thus, the term includes water per se and aqueous solutions and dispersions. For example, the aqueous medium may be a liquid bodily discharge, such as urine, menses, and saliva.

The term "w/o" means weight percent.

DETAILED DESCRIPTION

This invention pertains to using anionic polyelectrolytes as binding agents to reduce the solubility of cationic antimicrobial polyelectrolytes after application to a substrate. Ionic attraction between the oppositely-charged anionic stabilizing polyelectrolytes and antimicrobial cationic polyelectrolytes results in formation of a polyelectrolyte complex (PEC). Both the anionic and cationic polyelectrolytes are initially soluble in water or aqueous solutions, when the oppositely-charged polymer is not present. When solutions of the two types of polyelectrolytes are mixed, a PEC spontaneously forms. The PEC is either insoluble in water or aqueous solutions, or else the solubility is substantially reduced relative to the two individual polyelectrolytes. In a preferred embodiment, a treatment liquid comprising a stable colloid, suspension, dispersion, solution, coacervate, or emulsion of the PEC in an aqueous carrier is used to treat an absorbent substrate, thus fully or partially coating, infiltrating, or infusing the PEC onto or into the substrate. Subsequent drying results in a modified substrate which is coated/infused with the PEC. The PEC is thus bound to the substrate and is significantly less prone, than either of the component polyelectrolytes would be in the absence of the other, to being washed-off (out), leached, leaked, extracted, or migrated from the substrate during use, or when exposed to aqueous fluids or solvents. This happens primarily because the solubility of the PEC is lower than that of either polymer component. The modified substrate prepared in this manner exhibits antimicrobial properties, is biocompatible, and in a preferred embodiment may be utilized as a wound dressing material.

The unexpected observation has been made that subsequent treatment of dried antimicrobial article using ethylene oxide (EtO) results in improved performance properties of the antimicrobial article, even after the EtO is removed from the article.

It is known in the art to use cationic polyelectrolytes as antimicrobial agents. One class of such polyelectrolytes is quaternary ammonium polymers (also known as polyquats or polyquaterniums). In general, the cationic polyelectrolytes are soluble in water in the absence of a complexing agent such as an anionic polyelectrolyte. Thus, direct application of a cationic polyelectrolyte solution to a substrate, followed by drying will result in a treated substrate wherein the cationic polyelectrolyte can easily be removed by subsequent exposure to water or aqueous solutions. This is undesirable for two reasons. First, the active agent (cationic polyelectrolyte) is depleted, and thus efficacy will be reduced. Second, the active agent may migrate to a location which is not desirable. For instance, if the treated substrate is used as a wound dressing, the antimicrobial agent may migrate into the wound and interfere with wound healing or have toxic, or otherwise undesirable, effects. Thus, it is desirable to have a treated substrate wherein all or part of the cationic polyelectrolyte active agent is bound to the treated substrate in a permanent or non-leachable manner, and wherein the treated substrate is biocompatible or has no effect on the body.

It is an aspect of this invention to provide an antimicrobial article that has an antimicrobial cationic polyelectrolyte bound to it, wherein said antimicrobial article exhibits non-leachable antimicrobial properties. It is an aspect of this invention to provide an antimicrobial article that has an antimicrobial cationic polyelectrolyte bound to it, wherein said antimicrobial article is biocompatible. These materials are useful as antimicrobial wound dressings, medical devices, clothing, etc, or as components thereof.

It is an aspect of this invention to provide a method for forming a substrate that has an antimicrobial cationic polyelectrolyte bound to it. These materials are useful as antimicrobial wound dressings, medical devices, clothing, etc., or as components thereof.

It is an aspect of this invention to provide a method of manufacturing an antimicrobial article comprising all or part of a wound dressing, medical device, or clothing, that has an antimicrobial cationic polyelectrolyte bound to said article in a non-leachable manner, wherein the antimicrobial article is biocompatible and exhibits antimicrobial properties, and wherein said method manufacture includes conducting assays, tests, or measurements to verify, validate, demonstrate, or confirm that the antimicrobial article exhibits non-leaching antimicrobial properties, and/or is biocompatible. The non-leachable antimicrobial properties and biocompatibility are key to the safe and effective use of products manufactured from the antimicrobial article; hence, the assays, tests, or measurements to verify, validate, demonstrate, or confirm that the antimicrobial article exhibits non-leachable antimicrobial properties and biocompatibility is considered as significant and important steps in the manufacture of the antimicrobial article. The assays, tests, or measurements to verify, validate, demonstrate, or confirm that the antimicrobial article exhibits non-leachable antimicrobial properties may comprise testing for antimicrobial efficacy of the antimicrobial article, or testing for the presence of antimicrobial cationic polyelectrolyte remaining bound to the antimicrobial article after the treated substrate has been exposed to actual or simulated use conditions such as extraction or exposure to fluids. Suitable test methods include microbiological assays, dye tests, spectroscopy, colorimetry, or measurement of surface charge, such as zeta potential measurements. Alternatively, the assays, tests, or measurements to verify, validate, demonstrate, or confirm that the antimicrobial article exhibits non-leachable antimicrobial properties may comprise testing of an extract, rinsate, leachate, or other fluid which has been in contact with the antimicrobial article, to show a lack of antimicrobial activity therein, or an absence of appreciable antimicrobial cationic polyelectrolyte therein. The assays, tests, or measurements to verify, validate, demonstrate, or confirm that the antimicrobial article is biocompatible may comprise in-vivo or in-vitro assays such as cytotoxicity, irritation, sensitization, and the like.

It is known in the art to covalently bond cationic polyelectrolytes to surfaces in order to impart nonleaching antimicrobial activity; however, these methods generally require difficult processing conditions such as inert atmosphere, irradiation, reactive chemical intermediates, or use of toxic or flammable solvents. Alternatively, an excess of material is applied and non-bonded material is removed. This is wasteful of raw materials, and requires extra processing steps, such as washing/rinsing, which may disrupt the physical integrity of the substrate. The current invention requires simply combining aqueous solutions of the two polyelectrolytes to form a treatment liquid comprising a stable colloid, suspension, dispersion, solution, coacervate, or emulsion of a PEC in an aqueous carrier, applying the treatment liquid comprising a stable colloid, suspension, dispersion, solution, coacervate, or emulsion of the PEC in an aqueous carrier to the substrate, and then drying the treated substrate. There is no excess material applied, so washing or rinsing is not required. Also, the process is efficient and economical from a materials utilization standpoint. The process is also straightforward, quick, and compatible with common processes and equipment used in the textile and nonwovens industries.

It is known in the art that cationic and anionic polyelectrolyte in solution will spontaneously react to form a PEC. In order to be useful for the practice of this invention; however, the two polyelectrolytes are mixed in a controlled manner. The physical form of the PEC is affected by several factors including molecular weight of each component, solution concentration of each component, charge density of each component, order and rate of mixing, temperature, pH, and ionic strength of the solution. In order to be useful for treating a substrate, the PEC is mixed so that it remains evenly dispersed in the aqueous carrier as a stable dispersion, suspension, or emulsion. If the process is not done correctly, solids, precipitates, flocs, agglomerates, or particles of the PEC could be formed, and cause non-uniform coverage of the substrate, and can also interfere with proper operation of the processing equipment, or in some cases the PEC can even separate from the carrier as a distinct second liquid phase, which can deposit as an insoluble gummy residue which can be very difficult to remove from equipment due to poor solubility of the PEC. Such manifestations will also alter the concentration of active agent being applied to the substrate, which is undesirable. Lack of control in the formation of the PEC can also result in undesirable properties in the final product such as excessive stiffness, or uneven distribution of the applied material.

The antimicrobial effect of a cationic polyelectrolyte is achieved by electrostatic interaction of the positively-charged atoms present in the cationic polymer structure and the exterior of a microorganism, such as a bacterial cell. Since the same type of electrostatic interaction is responsible for the formation of the PEC, the ratio of anionic polyelectrolyte charges to cationic polyelectrolyte charges must be carefully controlled. Put another way, if all the positively-charged sites on the antimicrobial cationic polyelectrolyte were complexed with sites on the anionic stabilizing polymer, then there would be no positive sites left to function as antimicrobial agents. So, the ratio of cationic to anionic polyelectrolyte sites must be greater than 1 to 1. On the other hand, if the ratio is too high, then the PEC will tend to increase in solubility. Thus, it is an aspect of this invention that the ratio of polycationic charge to polyanionic charge is carefully controlled, and that said ratio is greater than 1 to 1, and preferably greater than 1.3 to 1, but less than approximately 2 to 1. In an example described below (Table 1, Sample BB), the cationic polyelectrolyte (PD) is used at 0.30 weight %, and the anionic polyelectrolyte (PAASS) is used at 0.10 weight %. The formula weight of PD monomer is 162, and the formula weight of PAASS is 94. Thus the molar ratio of cationic to anionic sites in this example is approximately (0.30/168)/(0.10/94)=1.67.

It is an aspect of this invention that the overall amount of the cationic polyelectrolyte in the a treatment liquid comprising a stable colloid, suspension, dispersion, solution, coacervate, or emulsion of the PEC in an aqueous carrier and in the finished treated material is controlled so as to maximize the antimicrobial efficacy of the material; however, too high a content of cationic polyelectrolyte could cause undesirable properties, such as toxicity due to a higher concentration of extractable cationic polyelectrolyte. Therefore, it is an aspect of this invention that the amount of cationic polyelectrolyte in the final material be controlled so that it provides high antimicrobial efficacy, but shows low toxicity or cytotoxicity. In a preferred embodiment of this invention the concentration of cationic polyelectrolyte in the finished treated material is between 0.01 and 1.0 w/o. In a more preferred embodiment, the concentration of cationic polyelectrolyte in the finished treated material is between 0.10 and 0.50 w/o, and in a most preferred embodiment the concentration of cationic polyelectrolyte in the finished treated material is between 0.2 and 0.35 w/o.

In a preferred embodiment of this invention the finished treated material is antimicrobial, and does not support the growth of microorganisms within the material, and when utilized as a wound dressing it is biocompatible (i.e. has "no effect on the body").

Examples of polyelectrolytes useful in the practice of this invention include, by way of illustration only, poly(ethylenesulfonic acid), poly(vinylsulfuric acid), poly(styrenesulfonic acid), poly(vinylphenylsulfuric acid), poly(vinyl-N-alkylpyridinium salt), poly(methylene)-N,N-dimethylpiperidinium salt, poly(vinylbenzyltrimethyl ammonium salt), poly(dimethyl diallyl ammonium chloride), poly(N,N,N',N'-tetramethyl-N—P-xylylenepropylene diammonium chloride), N-vinylpyrrolidone/dimethylaminoethyl methacrylate quaternized copolymer, poly(N-ethyl-4-vinylpyridinium bromide), poly(vinyl-butylpyridinium bromide), poly(methacryloxyethyl trimethyl ammonium bromide), poly(butyl acrylate-methacryl oxyethyl trimethyl ammonium bromide), and poly(vinyl-N-methylpyridinium bromide), poly(acrylic acid), poly(methacrylic acid), poly(maleic acid-co-alkene), poly(maleic acid-co-vinyl alkyl ether), poly(glutamic acid), poly(vinylamine), polyethyleneimine, chitosan, glycol chitosan, polylysine, sodium carboxymethyl cellulose, sodium carboxymethyl-hydroxyethyl cellulose, dextran sulfates, hyaluronic acid, heparin, chondroitin sulfate, poly(galacturonic acid), and poly(glutamic acid), and copolymers, blends, or mixtures of one or more of these.

In a preferred embodiment of this invention the cationic polyelectrolyte is a quaternary ammonium polymer or a quaternary ammonium copolymer. In a more preferred embodiment, the cationic polyelectrolyte is poly(diallyldimethylammonium chloride) (also known as polyDADMAC). In a preferred embodiment, the anionic polyelectrolyte is one or more selected from the group consisting of salts of poly (acrylic acid) and its derivatives or copolymers, and polystyrene sulfonate, or its derivatives or copolymers. In a more preferred embodiment, the cationic polyelectrolyte is poly(diallyldimethylammonium chloride) (also known as polyDADMAC), and the anionic polyelectrolyte is one or more selected from the group consisting of salts of poly(acrylic acid) and its derivatives or copolymers, and polystyrene sulfonate, or its derivatives or copolymers. In the most preferred embodiment, the cationic polyelectrolyte is poly(diallyldimethylammonium chloride) (also known as polyDADMAC), and the anionic polyelectrolyte is one or more selected from the group consisting of salts of poly(acrylic acid) and its derivatives or copolymers.

When polyDADMAC is used as the cationic polyelectrolyte in the practice of this invention an average molecular weight of greater than 50,000 is preferred. An average molecular weight of more than 100,000 is more preferred, and an average molecular weight of more than 200,000 is most preferred.

It is an aspect of this invention that the antimicrobial cationic polyelectrolytes comprise polymeric phosphonium compounds. Polymeric phosphonium compounds are known to possess antimicrobial properties. Several reports in the chemical literature concern the synthesis of various antimicrobial synthetic polymers. For example, the synthesis of polymeric phosphonium derivatives of styrene has been reported by Endo, T., et al in "*Novel Polycationic Biocides: Synthesis and Antibacterial Activity of Polymeric Phosphonium Salts*" (Journal of Polymer Science Part A: Polymer Chemistry, 31, pp. 335-342, 1993). Phosphonium quaternary polymers have been shown to be up to 4 orders of magnitude more effective as antimicrobial agents than the corresponding nitrogen quaternary polymers.

When the sodium salt of poly(acrylic acid) (abbreviated as PAASS) is used as the anionic polyelectrolyte in the practice of this invention, an average molecular weight of at least 20,000 is preferred. In a comparative example, PAASS with an average molecular weight of 2,000 did not result in the formation of a PEC with useful solubility properties.

When the sodium salt of poly(4-styrenesulfonic acid) (abbreviated as PSSA) is used as the anionic polyelectrolyte in the practice of this invention, an average molecular weight of at least 50,000 is preferred. An average molecular weight of at least 75,000 is more preferred.

In a preferred embodiment of this invention, the cationic polyelectrolyte is polyDADMAC and the anionic polyelectrolyte is PAASS, and the polyDADMAC concentration in the treatment liquid comprising a stable colloid, suspension, dispersion, solution, coacervate, or emulsion of the PEC is at least 0.10 w/o, but less than 0.50 w/o, and the PAASS concentration in the treatment liquid comprising a stable colloid, suspension, dispersion, solution, coacervate, or emulsion of the PEC is at least 0.025 w/o, but less than 0.20 w/o. In a more preferred embodiment of this invention, the cationic polyelectrolyte is polyDADMAC and the anionic polyelectrolyte is PAASS, and the polyDADMAC concentration in the treatment liquid comprising a stable colloid, suspension, dispersion, solution, coacervate, or emulsion of the PEC is at least 0.20 w/o, but less than or equal to 0.30 w/o, and the PAASS concentration in the treatment liquid comprising a stable colloid, suspension, dispersion, solution, coacervate, or emulsion of the PEC is at least 0.07 w/o, but less than or equal to 0.14 w/o.

It is an aspect of this invention that a solution of a cationic polyelectrolyte is mixed with a solution of an anionic polyelectrolyte. The mixing may be accomplished by combining two solutions followed by stirring or shaking. The solution concentrations of the anionic polyelectrolyte and cationic polyelectrolyte prior to mixing should be close to (i.e. no more than approximately 5 times that of) the final concentration desired in the stable colloid, suspension, dispersion, solution, coacervate, or emulsion of the PEC. In a preferred embodiment, the concentration of each the anionic and cationic polyelectrolyte is exactly twice that desired for each in the final stable colloid, suspension, dispersion, solution, coacervate, or emulsion of the PEC, and equal volumes of such solutions are combined to produce the final stable colloid, suspension, dispersion, solution, coacervate, or emulsion of the PEC.

It is an aspect of this invention that the pH of the stable colloid, suspension, dispersion, solution, coacervate, or emulsion of the PEC may be kept basic in order to ensure that the anionic polyelectrolyte is maintained in its fully-ionized form. The pH may be adjusted by addition of suitable acids or bases. The pH maybe adjusted prior to mixing the cationic and anionic polyelectrolyte solutions, or it may be adjusted after they are mixed. In a preferred embodiment of this invention, the pH of the stable colloid, suspension, dispersion, solution, coacervate, or emulsion of the PEC is from 8 to 10. The treatment liquid comprising a stable colloid, suspension, dispersion, solution, coacervate, or emulsion of the PEC in an aqueous carrier may be applied to the article using methods know in the art, including but not limited to, spraying, dipping, infusing, brushing, or rolling.

Excess treatment liquid may be removed by suitable methods known in the art, such as rolling, nipping, padding, centrifuging, wringing, or blotting, and the like, in order to control the amount of cationic polyelectrolyte in the final treated material. Any mechanical action or force may be applied; however, it is preferred that such action or force be uniform in order to provide an even distribution of remaining solution within the loaded substrate as the solution is forced out. It should be noted application of a mechanical force to remove excess solution prior to drying is distinct from the drying procedure in that the mechanical force removes both the antimicrobial and the carrier solution, while the drying procedure removes only the carrier solution, through evaporation, but leaves the antimicrobial in the loaded substrate.

It is an aspect of the inventive method to use any temperature and time combination that results in drying of said material. As used herein, dried means, for instance, that a substrate exposed to a solution of antimicrobial cationic polyelectrolytes is then dried to a constant weight. As used herein, dried to a constant weight means dried to the point at which continued application of the chosen drying procedure will no longer result in a considerable additional measurable loss of weight due to evaporation of water or other solvent. Attainment of constant weight is a useful tool to measure extent of dryness; however, the attainment of constant weight is not the actual factor that enables non-leachable attachment of the antimicrobial to the substrate. The particular temperatures and drying times necessary to achieve drying depend, among other things, on the particular substrate material, the initial amount of moisture in the article, the weight and size of the article, the amount of airflow provided to the article during drying, and the humidity of the air or other medium contacting the article. Any drying apparatus, drying method, and temperature and drying time combination that dries the treated substrate is sufficient. For purposes of illustration, depending on the particular characteristics of a particular application, the drying step may be performed in an oven (e.g. 80° C. for 2 hours), in a high throughput furnace (e.g. 140° C. for 30 seconds), in a clothes dryer, in a desiccator, in a vacuum chamber, in a dehumidifier, in a dehydrator, or in a lyophilizer (freeze dryer). Infrared heat, radiant heat, microwave, and hot air are all suitable drying methods for the substrate which has been exposed to a solution of antimicrobial cationic polyelectrolytes. The upper limit of drying temperature for a particular application will generally be determined by the degradation temperature of the particular substrate or antimicrobial cationic polyelectrolyte being treated.

It is an aspect of the current inventive method that a rinsing step may be optionally exercised on the dried material. It is possible that when utilizing a particular embodiment of the method of the current invention that only a portion of the total antimicrobial cationic polyelectrolytes applied to the substrate will actually become non-leachably bonded to the substrate, or is considered to be substantially unleachable from the substrate. In such instances, the inherently antimicrobial material may also contain some leachable antimicrobial cationic polyelectrolytes. The decision of whether or not to rinse the treated material will depend on whether a leaching antimicrobial property, in addition to the inherently non-leaching antimicrobial property, is desired in the final product. For some applications (e.g. textile applications), it may be desirable to retain some or all of the leachable portion of antimicrobial cationic polyelectrolytes in the final product, in combination with the non-leaching portion, because the leachable portion can contribute to the overall antimicrobial activity, at least initially, before the leachable portion becomes depleted. So, for example, where a particular application calls for retention of the leachable portion, it is suitable to utilize the inherently antimicrobial material after it has been thoroughly dried (without rinsing). For other applications, it may be desirable to remove the entire leachable portion and retain only the non-leaching portion. For example, where a particular application calls for removal of the leaching portion, the thoroughly dried treated material can be repeatedly rinsed in fluid to remove the leachable portion of antimicrobial cationic polyelectrolytes that did not attach to the substrate during the thorough drying step. In one exemplary embodiment, the rinsing step can be considered complete when conductivity readings of the rinsate equal that of the input rinse fluid, indicating that the rinsate is free of antimicrobial. In another exemplary embodiment, the rinsing can be accomplished by using a salt solution, followed by rinsing in fresh water to remove both the leachable antimicrobial and salt in order to obtain the lowest possible level of leachable antimicrobial. It is an aspect of this invention that the drying step is repeated after rinsing.

It is an aspect of this invention that the dried modified ("treated") substrate material of this invention may be sterilized by methods known in the art, including steam sterilization (autoclaving), gamma irradiation, and by ethylene oxide (EtO) sterilization, without compromising the nonleachable antimicrobial efficacy or biocompatibility of the treated article. The unexpected observation has been made that sterilization of treated substrates or antimicrobial articles using EtO results in enhanced antimicrobial efficacy of the treated substrates and antimicrobial articles when tested by methods described herein. Furthermore, improved antimicrobial efficacy of the treated substrate and antimicrobial articles, and improved resistance to the immobilized PEC against being washed-off (out), leached, leaked, extracted, or migrated from the antimicrobial article during use, or when exposed to aqueous fluids or solvents are obtained after subjecting the treated substrate to EtO sterilization. Therefore it is an aspect of this invention that the treated substrate is exposed to EtO in order to enhance the antimicrobial properties of the treated substrate. Terms such as "EtO treatment", "EtO sterilized", "EtO exposed", and similar characterizations may be used interchangeably in the description of this invention. Methods to expose the treated substrate to EtO will be familiar to one skilled in the art. Ethylene oxide is toxic and flammable, and due precautions must be taken. Standardized methods and procedures are used for EtO sterilization of medical devices, and in fact are required by government regulations, and any of these methods and procedures may be suitable for use in the practice of this invention. By way of example only, methods described in the following citations may be useful: *Requirements for validation and routine control—Radiation sterilization, AAMI/ISO* 11137; *Sterilization of healthcare products—Radiation Sterilization—Selection of a sterilization dose for single production batch, AAMI/ISO TIR No.* 15844; *Medical devices—Validation and routine control of ethylene oxide sterilization, AAMI/ISO* 11135; *Sterilization of medical devices Validation and routine control of ethylene oxide sterilization, EN*550 (*European standard*); *Biological evaluation of medical devices—Part* 7: *Ethylene oxide sterilization residues, AAMI/ISO* 10993-7; *Sterilization of medical devices—Microbiological methods, Part* 1: *Estimation of population of microorganisms on products, AAMI/ISO* 11737-1; *Sterilization of medical devices—Microbiological methods, Part* 2: *Tests of sterility performed in the validation of a sterilization process, AAMI/ISO* 11737-2; *Biological Evaluation of Medical Devices—Part* 7: *Ethylene Oxide Sterilization; ETO Residuals, ANSI/AAMI/ISO* 10993-7. Standard practice of EtO sterilization involves thorough degassing of sterilized materials to remove residual EtO; therefore, it is believed that residual EtO is not responsible for the enhanced antimicrobial efficacy observed in the practice of this invention. The actual mechanism for the enhancement of the properties of the materials of the current invention by EtO sterilization is unknown at this time. While Applicants do not wish to be bound by any theory of invention, it appears that the enhancement may be due to some type of rearrangement of the PEC, or redistribution of the PEC on the substrate surface caused by exposure to EtO. Since the EtO sterilization process involves multiple cycles of heat, pressure, humidity, and vacuum, it is plausible that one or a combination of these factors is responsible for the observed enhancement of properties rather than the actual exposure of the material to EtO. Since EtO is removed from the treated article as part of the EtO exposure process, the observed increase in efficacy is not due to the chemical action of residual EtO. It should also be noted that sterilization per se is likely not the key factor involved in the increase of efficacy observed after materials prepared by the methods of this invention have been exposed to EtO. Identical materials sterilized by either dry heat, steam sterilization (autoclaving), or UV exposure did not exhibit any change in antimicrobial efficacy.

It is an aspect of the current inventive method that it can establish a non-leaching attachment of antimicrobial cationic polyelectrolytes or antimicrobial polyelectrolyte complexes to a variety of substrates including natural, synthetic, and blended substrates and woven or non-woven textiles. Natural and synthetic substrate materials amenable to the current inventive method include, but are not limited to, cellulose, cellulose derivatives, paper, wood, wood pulp, microbially-derived cellulose, microcrystalline cellulose, hydroxyethyl cellulose, carboxymethyl cellulose, methyl cellulose, rayon, cotton, wood pulp, linen, polysaccharide, protein, wool, collagen, gelatin, chitin, chitosan, alginate, starch, silk, polyolefin, polyamide, fluoropolymer, polyvinyl chloride (PVC), vinyl, rubber, polylactide, polyglycolide, acrylic, polystyrene, polyethylene, polypropylene, nylon, polyester, polyurethane, and silicone, all of which may be verified by routine experimentation based on the present disclosure.

It is an aspect of this invention that the process of making the PEC-treated substrate does not require the use of an inert atmosphere, vacuum, high pressure, irradiation, organic solvents, catalysts, excessively high temperatures, and/or volatile, expensive, flammable, or toxic reagents to produce the antimicrobial material. This is in contrast to many prior methods of preparing antimicrobial articles which require such measures.

It is an aspect of the current inventive method that the antimicrobial activity exhibited by materials manufactured by the method is very robust. In contrast, some competing formulations, such as those marketed by AEGIS Environments, have been found to be inactivated after exposure to blood (see EP 0136900) or 10% fetal bovine serum. In one exemplary embodiment of the current inventive method, the antimicrobial activity of non-leachably attached polymeric molecules of the quaternary ammonium compound diallyldimethylammonium chloride remains robust in the presence of 10% fetal bovine serum, as described in the examples below. This aspect of the current inventive method will permit antimicrobial activity to persist in the presence of bodily fluids, which is a valuable and useful property for many applications in the health industry.

It is an aspect of this invention that silane, silicone, or siloxane antimicrobial cationic polyelectrolytes are not applied to the substrate or incorporated into the antimicrobial material, as silane, silicone or siloxane compounds generally will impart a water-repellent character to a substrate of composition, thus reducing the absorbency of the material.

It is an aspect of this invention that the antimicrobial article, or modified substrate material, will show a low concentration of extractable (leachable) cationic polyelectrolyte when tested as described herein. In a preferred embodiment of this invention, an extract of the antimicrobial article or modified substrate material prepared according to ISO standard method 10993-12 contains less than 100 ppm of cationic polyelectrolyte. In a more preferred embodiment of this invention, an extract of the antimicrobial article or modified substrate material prepared according to ISO standard method 10993-12 contains less than 60 ppm of cationic polyelectrolyte, and in a most preferred embodiment, an extract of the antimicrobial article or modified substrate material prepared according to ISO standard method 10993-12 contains less than 50 ppm of cationic polyelectrolyte. In general, saline solutions containing less than approximately 60 ppm of polyDADMAC do not cause skin irritation or cytotoxicity, In addition, in a preferred embodiment of this invention the material prepared by the method of this invention will be biocompatible and exhibit zero, or low, cytotoxicity when tested by the standard methods described herein.

It is an aspect of this invention that the antimicrobial materials prepared by the method of this invention will have significant antimicrobial activity against bacterial organisms. Preferably, the antimicrobial composition of the current invention is effective against Gram+ bacteria. More preferably, the antimicrobial of the current composition is effective against Gram+ bacteria, and Gram− bacteria. Most preferably, the antimicrobial of the current composition is effective against Gram+ bacteria, Gram− bacteria, and also fungal and/or viral organisms.

Antimicrobial efficacy may be measured by appropriate methods which will be familiar to one skilled in the art. In particular, a modified version of the American Association of Textile Chemists and Colorists (AATCC) Test Method 100 ("*Antibacterial Finishes on Textiles: Assessment of*"), a test designed to test antibacterial finishes of textile materials is useful, and is described in the following examples. One skilled in the art will recognize that a significant reduction in the number of viable bacteria should be observed when the antimicrobial material is tested according to this method, which utilizes a non-antimicrobial (untreated) material with similar physical properties as a "negative control". Preferably, the reduction in bacterial levels of both of the common bacterial species *Staph. aureus* and *E. coli* (tested separately vs. negative control: i.e. untreated substrate) should be a factor of 1000 (a "3-log kill", or 99.9% reduction). More preferably, the reduction in bacterial levels of both of the common bacterial species *Staph. aureus* and *E. coli* (tested separately vs. negative control: i.e. untreated substrate) should be a factor of 10,000 (a "4-log kill", or a 99.99% reduction). Even more preferably, the reduction in bacterial levels of both of the common bacterial species *Staph. aureus* and *E. coli* (tested separately vs. negative control: i.e. untreated substrate) should be a factor of 100,000 (a "5-log kill", or a 99.999% reduction). Most preferably, the reduction in bacterial levels of both of the common bacterial species *Staph. aureus* and *E. coli* (tested separately vs. negative control: i.e. untreated substrate) should be a factor of 1,000,000 (a "6-log kill", or 99.9999% reduction). It should be noted that limitations of the test method may result in lower numerical reductions of bacterial levels if the number of viable bacteria in the negative control is low. For instance, if the negative control contains only 500 viable bacteria (colony forming units), a reduction factor of 500 (a 2.7-log kill) is the maximum possible result; however, in this case the result represents a 100% reduction of bacterial population, and is perfectly acceptable. Generally, when the standard method is followed using absorbent textile test articles, the growth of most commonly-encountered bacteria in the negative control will be in the range of 100,000 to 10,000,000 colony forming units.

The solution of the cationic polyelectrolyte and the solution of the anionic polyelectrolyte are mixed under conditions adapted to result in the formation of a polyelectrolyte complex. Such conditions typically include mixing at ambient temperature, although it is not necessary to do so. Such conditions also include intense mixing, such as sonication, high-shear mixing, and the like. The amounts of the two solutions to be mixed depend upon the concentration of polyelectrolyte in each solution and the desired molar ratio of cationic polyelectrolyte to anionic polyelectrolyte.

The stable colloid, suspension, dispersion, solution, coacervate, or emulsion of the PEC in an aqueous carrier which results from the mixing step may be used for coating the substrate. That is, it is not necessary to isolate the polyelectrolyte complex in a solvent-free condition and redissolve it. The surface of the substrate is contacted with the stable colloid, suspension, dispersion, solution, coacervate, or emulsion of the PEC in an aqueous carrier under conditions sufficient to result in the coating of the surface of the substrate with the polyelectrolyte complex. Again, such conditions typically involve ambient temperature and a degree of spreading force sufficient to spread the solution of the nonstoichiometric polyelectrolyte complex over the surface of the substrate. When the substrate is a film, the requisite degree of spreading force may be achieved, for example, by spreading the solution of the polyelectrolyte complex on the surfaces of the film by means of a doctor blade or Meyer rod. Soaking the film in the stable colloid, suspension, dispersion, solution, coacervate, or emulsion of the PEC in an aqueous carrier with ultrasonic agitation also may be employed. When the substrate is a fibrous web, sufficient spreading force may be achieved by agitating the substrate in the solution of the nonstoichiometric polyelectrolyte complex, forcing the solution or a foam thereof through the fibrous web by means of suction or pressure, and passing the web saturated with the solution of the nonstoichiometric polyelectrolyte complex through a nip formed by a pair of compression rolls.

For treatment of woven and nonwoven textile substrates according to the practice of this invention, the nominal wet pickup rate (damp weight) of a dry textile exposed to the treatment liquid followed by expulsion of excess liquid using methods described herein will generally be between approximately 75% and 125%; although higher and lower values can also be useful. In other words, one pound of an initially dry textile substrate will generally weigh between 1.75 and 2.25 pounds after treatment with the treatment liquid comprising a stable colloid, suspension, dispersion, solution, coacervate, or emulsion of the PEC, prior to being dried. It will be understood by one skilled in the art that using a higher/lower wet pickup rate will result in a higher/lower content of antimicrobial being added to the treated substrate, and that it is possible to compensate by using a treatment liquid with a lower/higher concentration of PEC, in order to achieve a desired level of antimicrobial in the treated substrate. Thus, the levels and concentrations of polymers cited in the examples and embodiments described herein may be adjusted accordingly. For instance, it may be desirable to utilize a low wet pickup rate for a particular application, as this will allow more economical drying of the treated substrate. In such a case, a more concentrated treatment liquid would be desirable.

It is an aspect of this invention that additives such as UV inhibitors, processing aids, softeners, antistatic agents, colorants, dyes, indicators, drugs, oils, lubricants, microspheres, temporary visual indicators, nutrients, growth factors, vitamins, emollients, moisturizers, scents, perfumes, emulsifiers, and the like may be added to the substrate in combination with the PEC, or be incorporated into the treatment liquid comprising a stable colloid, suspension, dispersion, solution, coacervate, or emulsion of the PEC in an aqueous carrier.

In light of the general disclosure provided herein above, with respect to the manner of practicing this inventive method, those skilled in the art will appreciate that this disclosure enables the practice of the inventive method as defined in the attached claims. However, the following experimental details are provided to ensure a complete written description of this invention, including the best mode thereof. However, it will be appreciated that the scope of this invention should not be construed in terms of the specific examples provided. Rather, the scope of this invention is to be apprehended with reference to the claims appended hereto, in light of the complete description of this inventive method constituted by this entire disclosure.

It is to be understood that the present invention may have various other embodiments. Furthermore, while the form of the invention herein shown and described constitutes a preferred embodiment of the invention, it is not intended to illustrate all possible forms thereof. It will also be understood that the words used are words of description rather than limitation, and that various changes may be made without departing from the spirit and scope of the invention disclosed. The scope of the invention should not be limited solely to the examples given.

EXAMPLES

Materials
The following materials were used in the preparation of samples described in the following Examples.

Substrates:
"240 gsm": A needle punched composite nonwoven, consisting of a polyolefin based wound contact layer and a viscose based absorbent core, having the following composition: viscose (rayon) fibres based from EFC or TFC pulp [CAS no 68442-85-3; approx: 90%] and polyolefin bi-components fibres [CAS no 9003-07-0(PP)/9002-88-4 (PE); approx:10%], with an approximate density of 240 grams per square meter (gsm), and a thickness of 1.7 to 2.3 mm.
"115 gsm": A thermobonded, needle-punched, composite nonwoven consisting of a polyolefin based wound contact layer and a viscose based absorbent core, having the following composition: 43% viscose (rayon) fibres (CAS No. 68442-85-3) and 57% polypropylene (CAS No. 9003-07-0), with a thickness of 0.95 to 1.25 mm, and a density of approximately 115 grams per square meter (gsm).
"CG": Dutex® cotton gauze (manufactured by Dumex Medical, Canada, Inc.).
Polymers:
"PD": Poly(diallyldimethylammonium chloride), also abbreviated "polyDADMAC", supplied by MV Products, Inc. (St. Louis, Mo.), SNF, Inc., Axchem #AF-6545, 40 wt % aqueous solution, "high viscosity", MW approximately 250,0000 g/mole.
"PAA1": Poly(acrylic acid)-sodium salt, supplied by Aldrich Chemical Co. (Milwaukee, Wis.), catalogue #41,604-5, CAS#[9003-04-7], 40 wt % aqueous solution, MW approximately 30,000.
"PAA2": Poly(acrylic acid)-sodium salt, supplied by Aldrich Chemical Co. (Milwaukee, Wis.), catalogue #420344, CAS#[9003-04-7], powder, MW approximately 2,100.
"PAA3": Poly(acrylic acid)-sodium salt, supplied by MV Products, Inc. (St. Louis, Mo.), SNF "Flosperse FS 10,000", CAS#[9003-04-7], 29 wt % aqueous solution, MW approximately 50,000.
"PSSA": Poly(4-styrenesulfonic acid), 18 wt % aqueous solution, supplied by Aldrich Chemical (Milwaukee, Wis.), catalogue #561223, CAS#[28210-41-5], MW approximately 70,000.
Note: In the following examples, pH of solutions were adjusted using either 3M potassium hydroxide (KOH), or 3M hydrochloric acid (HCl), and pH was determined using a Corning model 320pH meter calibrated with appropriate buffer solutions.

Example 1

Treatment of Substrates with a Cationic Polyelectrolyte (Comparative Example)

This example shows the preparation of wound dressing using antimicrobial cationic polymer and without anionic stabilizing polymer. One hundred grams of a solution of 0.3% PD was prepared and the pH was adjusted to 9.5. A sample of 240 gsm substrate weighing 18.91 grams was immersed in the solution, and then rolled through a hand-driven roller press to expel excess liquid. The damp weight of the material was 45.51 g (wet pickup of 141%). The material was laid flat and dried in an oven at 80° C. for approximately two hours, and designated as Sample X1. Colorimetric measurements indicated an average cationic polymer concentration of 130 ppm for an extract of this material which was prepared and tested using methods described herein. Using cytotoxicity testing methods described herein, this sample is found to have cytotoxic properties (see Table 7, below).

Example 2

Treatment of Substrates with PEC of polyDADMAC and Poly(Acrylic Acid)-Sodium Salt The following is a typical example of treating a nonwoven substrate using a PEC. A mixture of 15 g PD (40%) and 585 g water was stirred until thoroughly mixed. Separately, a mixture of 5 g PAA1 (40%) and 195 g water was stirred until thoroughly mixed. The pH of this second mixture was adjusted to 10.3 using 3M KOH. These solutions were then mixed together with rapid stirring to produce a milky-white liquid, with a pH of 9.0, a PD concentration of 0.30%, and a PAA concentration of 0.13%. A sample of 240 gsm substrate material weighing 184.7 g was immersed in this liquid for several minutes and then passed through a hand-driven roller press to expel excess liquid. The damp weight of the substrate after pressing was 489.1 g (wet pickup of 165%). This sample was then dried in an oven at 80° C., and designated as Sample BB. Other samples were prepared using the same process with slight variations. In some cases, a hand-driven roller was used, and in others, a motorized roller press was utilized. The substrate and percent wet pickup were also varied. Cationic and anionic polymers were varied in composition, ratio, and concentration. In all cases, the pH of the final treatment solution was adjusted to be between 9.0 and 10.0. In some cases pH was adjusted before solutions were combined, and in other cases the pH was adjusted after they were combined. In general, it is preferable to adjust each solution separately, prior to combination. The relative volumes of the two solutions were also varied, but in general it is preferable to mix equal volumes of solutions, with each being twice the final desired concentration of ingredients. A summary of various examples and processing conditions is given in Table 1 below, along with sample codes and the average concentration of cationic polyelectrolyte in an extract of the sample determined by methods described herein:

TABLE 1

Examples and Processing Conditions

| Sample Code | Cationic (%) | Anionic (%) | Substrate | Pick-up | Extract |
|---|---|---|---|---|---|
| BB | PD (0.30%) | PAA1 (0.10%) | 240 gsm | 165% | 90 ppm |
| CC | PD (0.30%) | PAA1 (0.13%) | 240 gsm | 154% | 55 ppm |
| FH | PD (0.30%) | PAA1 (0.10%) | 240 gsm | 165% | 51 ppm |
| FM | PD (0.24%) | PAA1 (0.09%) | 240 gsm | 173% | 41 ppm |
| FL | PD (0.20%) | PAA1 (0.07%) | 240 gsm | 165% | 38 ppm |
| GG | PD (0.15%) | PAA1 (0.065%) | 240 gsm | 165% | 48 ppm |
| GG2 | PD (0.15%) | PAA1 (0.065%) | 115 gsm | 209% | 48 ppm |
| X1 | PD (0.30%) | 0 (PD only) | 240 gsm | 141% | 130 ppm |
| X2 | PD (0.25%) | PAA3 (0.092%) | 240 gsm | 121% | 39 ppm |
| X2B | PD (0.25%) | PAA3 (0.092%) | 115 gsm | 139% | 36 ppm |
| X4 | PD (0.30%) | PAA3 (0.11%) | 240 gsm | 118% | 54 ppm |
| X4B | PD (0.30%) | PAA3 (0.11%) | 115 gsm | 154% | 61 ppm |
| X5 | PD (0.30%) | PAA3 (0.13%) | 240 gsm | 128% | 41 ppm |
| D1 | PD (0.30%) | PAA3 (0.11%) | CG | 120% | 37 ppm |
| X6 | PD (0.30%) | PAA1 (0.13%) | 240 gsm | 90% | 40 ppm |
| X6B | PD (0.30%) | PAA1 (0.13%) | 115 gsm | 117% | 31 ppm |
| EE | PD (0.30%) | PAA1 (0.15%) | 240 gsm | 157% | — |
| Y2A | PD (0.30%) | PAA2 (0.075%) | 240 gsm | 130% | 38 ppm |
| M2 | PD (0.30%) | PAA1 (0.075%) | 240 gsm | 121% | 99 ppm |
| MW | PD (0.30%) | PSSA (0.15%) | 240 gsm | 118% | 47 ppm |

It was observed that using a PAA to PD weight ratio of greater than about 0.5 (i.e. 0.15% PAA and 0.30% PD, as in sample EE) gave less than desirable results, as the treatment solution for sample EE left a sticky residue on the mixing containers, and on the press roller—indicating that some phase separation had occurred. This insoluble residue was difficult to remove, even by scrubbing. In addition, the substrate treated with this composition was found to be stiff, with a "scratchy" feel after drying. Such properties are undesirable in a wound dressing; however, they could be beneficial in other applications. The ratio at which these undesirable effects occur depends somewhat on the exact composition of the individual polymeric components. For instance, sample MW (using PSSA instead of PAASS) was also prepared using an anionic to cationic ratio of 0.5, but no undesirable effects were observed. On the other hand, similar undesirable effects were observed at a PAASS/PD ratio of only 0.43 (Sample X5) when higher MW PAASS was used. The ratio of anionic to cationic polymer at which undesirable effects are manifested is dependent on the chemical identity of the polymer, and also their molecular weights. While it is convenient to characterize these ratios in terms of weight, they could also be characterized by their relative electrostatic charge balance. It is an aspect of this invention that the ratio of the anionic to cationic polymers is as high as possible (in order to promote good binding of the cationic antimicrobial), but below that which causes precipitation of the PEC, lower antimicrobial efficacy, or which causes other undesirable effects.

The nitrogen (N) contents of various samples described above were determined by methods described herein (N-Kjeldahl). The amount of PD in the treated samples was calculated based on the % wet pickup and the concentration of PD in the treatment solution (Calc % PD). The amount of nitrogen expected in the treated samples (Calc ppm N) was calculated based on the inherent nitrogen content of PD (8.6%). The nitrogen content of an untreated 240 gsm substrate was measured, and subtracted from the measured values (N-Kjeldahl), to give the actual amount of nitrogen added during processing (N-corrected). The error between the calculated value and the measured value was calculated (N error). Results are shown in Table 2.

TABLE 2

Determination of Nitrogen Content of Various PD Samples

| Sample ID | Calc % PD | Calc ppm N | N-Kjeldahl | N-corrected | N error |
|---|---|---|---|---|---|
| 240 gsm | 0.00% | 0 | 45 | 0 | 0% |
| CC | 0.46% | 396 | 549 | 504 | 27% |
| FL | 0.26% | 227 | 313 | 268 | 18% |
| FM | 0.33% | 284 | 380 | 335 | 18% |
| FH | 0.42% | 357 | 524 | 479 | 34% |
| X6 | 0.27% | 232 | 414 | 369 | 59% |

(N values are given in ppm, based on dry weight of material)

Various samples described above were subjected to antimicrobial efficacy testing as described herein. In addition, selected samples sterilized by EtO sterilization utilizing methods described herein, were evaluated for antimicrobial efficacy. Surprisingly, it was discovered that most materials increased significantly in antimicrobial efficacy after being subjected to EtO sterilization. This effect was most apparent when tested against *pseudomonas* (PA). Results are summarized in Table 3, and the effect of EtO treatment is indicated for some samples.

TABLE 3

Antimicrobial Efficacy Results

| Sample ID | Log Kill | Species |
|---|---|---|
| CC | 3.6 (no EtO) | PA |
|  | 6.5 (EtO) | PA |
|  | 7.9 (EtO) | EC |
|  | 8.3 (no EtO) | EC |
| X1 | 4.9 (no EtO) | PA |
| X2 | 5.5 (no EtO) | PA |
| X2B | 6.63 (no EtO) | PA |
| X4B | 4.4 (no EtO) | PA |
| X5 | 3.6 (no EtO) | PA |
| Y2A | 6.0 (no EtO) | EC |
|  | 5.1 (no EtO) | PA |
| M2 | 4.0 (no EtO) | PA |
| FL | 3.2 (no EtO) | PA |
|  | 3.6 (EtO) | EC |
| EM | 3.6 (no EtO) | PA |
|  | 7.9 (EtO) | EC |
| MW | 4.6 (no EtO) | PA |
|  | 7.2 (no EtO) | EC |
| D1 | 3.3 (no EtO) | PA |
|  | 7.6 (no EtO) | SA |
|  | 4.5 (no EtO) | EC |
| FH | 4.4 (no EtO) | PA |
|  | 5.3 (EtO) | EC |
| X6 | 3.4 (no EtO) | PA |
| GG | 2.27 (no EtO) | PA |
|  | 6.9 (EtO) | PA |

Additional antimicrobial efficacy data is presented in Table 4.

TABLE 4

Antimicrobial Efficacy for sample CC (after EtO Sterilization) against various organisms, tested according to methods described herein.

| Organism | ATCC number | Average log reduction 240 gsm pad after 24 h | Sample Size | Standard Deviation |
|---|---|---|---|---|
| Staphylococcus aureus | ATCC 6538 | 7.44 | 6 | 0.88 |
| MRSA (Methicillin resistant S. aureus) | ATCC BAA-44 | 5.64 | 3 | 0.00 |
| Staphylococcus epidermis | ATCC 12228 | 8.17 | 6 | 0.00 |
| Pseudomonas aeruginosa | ATCC 15442 | 6.45 | 6 | 0.92 |
| Enterococcus faecalis | ATCC 10741 | 6.20 | 6 | 0.00 |
| Escherichia coli | ATCC 15597 | 7.88 | 6 | 0.41 |
| Enterobacter cloacae | ATCC 13047 | 7.37 | 3 | 0.92 |
| Proteus mirabilis | ATCC 7002 | 6.43 | 6 | 0.86 |
| Klebsiella pneumoniae | ATCC 13883 | 7.41 | 6 | 0.41 |
| Streptococcus bovis | ATCC 43143 | 4.60 | 3 | 0.26 |
| Streptococcus pyogenes | ATCC 10096 | 6.90 | 3 | 0.58 |
| Acetinobacter baumanni | ATCC 19606 | 5.61 | 3 | 0.51 |
| Serratia marcescens | ATCC 13880 | 7.73 | 6 | 1.11 |

Example 3

Demonstration of Insolubility of Dried PEC Film

A stable dispersion of PEC in an aqueous carrier was prepared as described for the treatment solution given in Example 2. Approximately 10 mL of this solution was poured onto a glass petri dish, and then dried in an 80° C. oven overnight. Upon drying, a clear hard film was formed on the surface of the glass petri dish. When submerged in water, this film became cloudy and soft; however, it did not dissolve, break, or become detached from the glass surface. This demonstrates the insoluble nature of the PEC.

Test Methods for Characterization of Antimicrobial Materials:

Materials produced as described in the above examples were characterized and tested for antimicrobial efficacy and biocompatibility according to the following methods. Note that these standard methods may be written in either past, present, or future tense; however it will be understood that these were the methods followed during the inventive process.

A. Microbiological Method to Verify the Antimicrobial Property of Treated Substrate Materials in the Presence of Serum Antimicrobial activity of materials prepared using the various methods and embodiments of this invention were assayed using a modified version of the American Association of Textile Chemists and Colorists (AATCC) Test Method 100 ("*Antibacterial Finishes on Textiles: Assessment of*"), a test designed to test antibacterial finishes of textile materials. Overnight cultures (ONC) of test microorganisms were generated in appropriate culture medium using standard methods. Using the ONC, an inoculum solution was prepared containing the test microorganism diluted to ~$10^6$ CFU/ml in phosphate buffered saline (PBS) and fetal bovine serum (FBS), at 10% v/v. Treated substrate materials (samples) and untreated substrate control materials (controls) were cut into 2.5 cm squares and autoclaved at 121° C. for 30 minutes to eliminate pre-existing microbial contamination. After autoclaving, samples and controls were allowed to cool for 15 minutes at room temperature. Samples and controls were each inoculated with 500 μL of inoculum and incubated at 37° C. in sterile covered petri dishes. After 18 to 24 hours incubation, the samples and controls were harvested with sterile forceps, placed into separate 15 mL tubes containing 15 mL PBS, and vortexed for 30 seconds to suspend any remaining viable microorganisms into solution. Appropriate tenfold dilutions of these suspensions were made using PBS solution and spread onto bacteria culture plates containing growth medium appropriate for the desired organisms and then incubated overnight at 37° C. After overnight culture, colonies growing on each plate are enumerated to determine antimicrobial efficacy. Data are reported as % killed or log reduction as compared to untreated controls inoculated with the same bacterial load, and incubated for the same length of time. It is convenient to express the efficacy of a particular formulation against a particular bacterial species as "log kill", "log reduction", or simply "LR". In the following discussions, a complete kill (i.e. 100% reduction of viable bacteria) will be denoted by using an asterisk after the LR number (6.0*, for example). The individual values of LR for each replicate of a given sample are calculated relative to the average colony count for the control sample with the same inoculation load and incubation time. The individual LR values for each replicate are then averaged, and the average LR is reported as the result. The dilution, spreading, plating and enumeration were conducted using standard microbiological techniques.

It is known based on previous experience of the inventors that the antimicrobial efficacy of cationic polyelectrolytes immobilized on absorbent surfaces varies against different bacterial species, and that cationic polyelectrolytes are generally more effective against Gram-positive bacterial species than against Gram-negative bacterial species. Furthermore, it is known that *Staph. aureus*, or SA (a Gram-positive species) is perhaps the most susceptible of commonly-encountered organisms. Likewise, *Pseudomonas aeruginosa*, or "PA" (a Gram-negative species) is one of least susceptible to cationic polyelectrolytes immobilized on absorbent surfaces. In general, most other commonly-encountered organisms, such as *E. coli,* or EC (a Gram-negative species) will fall between these two extremes in terms of susceptibility to cationic polyelectrolytes immobilized on absorbent surfaces. In other words, if a material prepared by the method of this invention is found to have high efficacy against PA (a LR of 6, for example), then it is very likely to have even higher efficacy against SA (a LR of 8, for example), unless the efficacy against PA is "full kill", which represents 100% deactivation, and thus cannot be exceeded. Conversely, it is not really possible to draw conclusions as to the efficacy against less susceptible organisms based on performance against more susceptible organisms. Thus, it is possible to conserve time and resources by first testing the formulations against less susceptible organisms such as PA, because at less than full kill conditions, a relative efficacy can be determined between various compositions.

B. Biocompatibility Testing Methods:

Three kinds of experiments were performed to aid in the testing of the biocompatibility of the materials produced by the method of this invention to prove that the samples will not have an effect on the body. These experiments were the following:

1. ASTM F895-84,

"Standard Test Method for Agar Diffusion Cell Culture Screening for Cytotoxicity." This assay is also comparable to methods outlined in ISO-10993-5, *"Biological Evaluation of Medical Devices"*. These assays were performed by Biological Consulting Services, Inc. in Gainesville, Fla.

2. ASTM F813-83,

"Standard Practice for Direct Contact Cell Culture Evaluation of Materials for Medical Devices." This assay was performed to determine qualitative biocompatibility data for the materials produced by the method of this invention. The assay is performed by placing the treated substrates directly on the test cells and measuring zones of cells affected. "CellTiter 96 Aqueous One Solution Cell Proliferation Assay" was additionally used as a supplement to ASTM F813-83 as a quantitative way to measure the cell viability.

3. "Contact Test".

These tests were designed to show no antimicrobial activity on bacteria by the contact layer of the materials produced by the method of this invention. The contact layer of the materials is placed on a lawn spread of bacteria, saturated with PBS to saturation level, and evaluated for growth on the material. These assays were performed at Quick-Med Technologies.

C. Extractability, Leaching, and Characterization Test Methods:

1. Extraction Method for Leachability Testing (QMT Method EX-1):

This method is to be used to prepare extracts for determination of leachable components of wound dressing materials. It is based on the standard conditions of time, temperature and ratio of sample to liquid extractant that is specified for cytotoxicity testing by ISO 10993-12, and it is representative of the conditions expected during actual use of the dressing. Material shall be dry and equilibrated with ambient temperature and humidity for one hour prior to testing. A ratio equivalent to 1.0 gram of material to 20 mL of extraction medium shall be used. The extraction medium shall be 1× phosphate buffered (pH=7.4) saline solution (PBS). Extraction shall be carried out in clean sterile sealed PE or PP culture tubes. Fifteen mL tubes shall be used for extraction volumes up to 10 mL. Fifty mL tubes maybe used for extraction volumes up to 40 mL. Test sample shall be weighed to nearest 0.01 gram and placed into the extraction tube containing the appropriate amount of PBS. A clean stainless steel spatula or glass rod shall be used to ensure that the sample is completely immersed into the PBS liquid. The sealed extraction tubes are placed into an incubator set at 37° C. (+/−2° C.) for 24 hours (+/−1 hour). The sample is decanted into a clean syringe and filtered through a 0.22 μm filter in order to ensure sterility, and then stored in a sealed sterile culture tube.

2. Colorimetric Method for Determination of Cationic Polymer in an Extract (QMT Method COL-1):

This method is to be used to determine the concentration of cationic polymer in aqueous solutions. This method is based on a standard method provided by Protech General Contracting Services, *"DISSOLVED POLYMER COAGULANT DETERMINATION-DADMAC"*, which utilizes a standard analytical "kit" available from GE Betz (DR2010/DR2000). The attached method (described above) shall be used with the following modifications:

A Spectronic-20 spectrophotometer shall be used instead of the specified instrument for measurement of absorbance at 575 nm. One centimeter path length polystyrene cuvettes shall be used instead of the specified 25 mL sample cell. Test samples and standards shall be mixed with reagents in 50 mL PP conical culture tubes, and an appropriate amount of solution transferred to the polystyrene cuvette for measurement.

A calibration curve was constructed using polyDADMAC (PD) standard solutions prepared by appropriate dilution of Axchem AF6545 40% polyDADMAC solution with 1× phosphate buffered (pH=7.4) saline solution (PBS). It was determined that the useful range of this method extends from approximately 0.5 to 10 ppm PD (see attached), with a linear range covering approximately 0.5 to 5.0 ppm PD.

Standard solutions shall be prepared by appropriate dilution of Axchem AF6545 40% polyDADMAC solution using 1× phosphate buffered (pH=7.4) saline solution (PBS). It is suggested that standard solutions of 0, 1, 2, and 4 ppm [PD] be prepared. According to the procedure, the 0 ppm solution will have an absorbance value of zero.

Sample solutions (such as extracts prepared using method QMT EX-1) shall be analyzed according to the procedure described above. Sample solutions with absorbance values higher then than 0.40 absorbance units shall be rejected. New aliquots of these samples shall be diluted appropriately using PBS solution, and the measurement repeated, including addition of new reagents. DO NOT DILUTE THE COLORED SOLUTION. The dilution factor shall be recorded, and used to calculate the actual [PD] based on comparison to absorbance values for standard solutions. All samples shall be exactly 25 mL (including any dilution) before addition of the reagents. For example, a 50 ppm solution of polyDADMAC should be diluted by mixing 1.0 mL of the solution with 24 mL of PBS prior to addition of reagents. This gives a dilution factor of 25×, and a [PD] of 2 ppm. The approximate absorbance of such a solution would be 0.15 absorbance units.

The concentration of PD in the sample shall be determined by numerical linear interpolation of the absorbance readings of the two standard solutions which have absorbance readings closest to that of the sample, such that one standard shows higher absorbance and one shows lower absorbance. One of the standards used must be within 0.1 absorbance unit of the sample; otherwise, an additional standard must be used.

3. Determination of Nitrogen Content (Kjeldahl Method):

In a preferred embodiment, the antimicrobial cationic polyelectrolytes used in the practice of this invention are quaternary ammonium compounds, and thus contain nitrogen. Samples of the treated substrate materials and of extract solutions prepared by the methods described herein were sent to Galbraith Laboratories (Knoxville, Tenn.) for Nitrogen Analysis by Kjeldahl Method (E7-1 Rev 10). This method gives the result in parts-per-million (ppm) of nitrogen. The background nitrogen content of untreated substrates must be subtracted from the measured value in order to determine the concentration of nitrogen in the sample. In a preferred embodiment of this invention, polyDADMAC is utilized as the cationic polyelectrolyte antimicrobial. The nitrogen content of polyDADMAC is 8.6% by weight, based on the molecular formula. The concentration of polyDADMAC in the sample can thus be calculated by dividing the measured ppm N result by 0.086.

Results of Antimicrobial Efficacy and Biocompatibility Testing:

1. ASTM F895-84

Standard Test Method for Agar Diffusion Cell Culture Screening for Cytotoxicity: Displayed below are two sets of tables, Table 5 displays the actual zones of cell lysis and Table 6 displays the results of the agar overlay/diffusion.

TABLE 5

Lysis Chart (Scoring Criteria)

| Zone Index | Description of Zone |
|---|---|
| 0 | No Detectable zone around or under specimen |
| 1 | Zone limited to area under specimen |
| 2 | Zone extends less than 0.5 cm beyond specimen |
| 3 | Zone extends 0.5 to 1.0 cm beyond specimen |
| 4 | Zone extends greater than 1.0 cm beyond specimen but does not involve entire dish |
| 5 | Zone involves entire dish |

| Sample | Zone Description Following 24 Hour Incubation | | | | | | Zone Description Following 48 Hour Incubation | | | | | |
|---|---|---|---|---|---|---|---|---|---|---|---|---|
| FM | 0 | 0 | 0 | 0 | 0 | 0 | 1 | 1 | 0 | 0 | 0 | 0 |
| FH | 0 | 0 | 0 | 0 | 0 | 0 | 0 | 0 | 0 | 0 | 0 | 0 |
| CC (EtO) | 0 | 0 | 0 | 0 | 0 | 0 | 0 | 0 | 0 | 0 | 0 | 0 |
| CC (before EtO) | 0 | 0 | 0 | 0 | 0 | 0 | 0 | 0 | 0 | 0 | 0 | 0 |
| (−) control | 0 | 0 | 0 | 0 | 0 | 0 | 0 | 0 | 0 | 0 | 0 | 0 |
| (+) control | | | 3 | | | | | | 5 | | | |

TABLE 6

Agar Overlay Chart (Scoring Criteria)

| Zone Index | Description of Zone |
|---|---|
| 0 | No observable cytotoxicity |
| 1 | Less than 20% of zone affected |
| 2 | 20 to 39% of zone affected |
| 3 | 40 to 59% of zone affected |
| 4 | 60 to 80% of zone affected |
| 5 | Greater than 80% of zone affected |

| Sample | Zone Description Following 24 Hour Incubation | | | | | | Zone Description Following 48 Hour Incubation | | | | | |
|---|---|---|---|---|---|---|---|---|---|---|---|---|
| FM | 0 | 0 | 0 | 0 | 0 | 0 | 1 | 1 | 0 | 0 | 0 | 0 |
| FH | 0 | 0 | 0 | 0 | 0 | 0 | 0 | 0 | 0 | 0 | 0 | 0 |
| CC (EtO) | 0 | 0 | 0 | 0 | 0 | 0 | 0 | 0 | 0 | 0 | 0 | 0 |
| CC (no EtO) | 0 | 0 | 0 | 0 | 0 | 0 | 0 | 0 | 0 | 0 | 0 | 0 |
| (−) control | 0 | 0 | 0 | 0 | 0 | 0 | 0 | 0 | 0 | 0 | 0 | 0 |
| (+) control | | | 5 | | | | | | 5 | | | |

2. Direct Contact/Cell Proliferation Assay Results:

According to the ASTM F813-83 requirements, the test articles were positioned directly onto the cellular monolayer. The microscopic examination of the cells both surrounding and under the tested samples after removal demonstrates the extent of biocompatibility. The results are summarized below in Table 7. Phenol was used as a positive (+) control while untreated substrate material was used a negative (−) control. Undisturbed cellular monolayer was used as a blank control. Description of the size of zone of cell lysis surrounding the dressing material or located directly under the samples has the following designations:

TABLE 7

Direct Contact/Cell Proliferation Assay Results

| Score | Description of Zone |
|---|---|
| 0 | No observable cytotoxicity |
| 1 | Less than 20% of zone affected |
| 2 | 20 to 39% of zone affected |
| 3 | 40 to 59% of zone affected |
| 4 | 60 to 80% of zone affected |
| 5 | Greater than 80% of zone affected |

| Sample | Zone description surrounding the specimen | | | Zone description under the specimen | | |
|---|---|---|---|---|---|---|
| CC (EtO) | 0 | 0 | 0 | 1 | 1 | 1 |
| FH | 2 | 0 | 0 | 1 | 2 | 1 |
| FM | 0 | 0 | 0 | 1 | 1 | 1 |
| X1 | 2 | 2 | 3 | — | — | — |
| (−) Control | 0 | 0 | 0 | 1 | 1 | 1 |
| (+) Control | 3 | 3 | 3 | 5 | 5 | 5 |

The results showed good biocompatibility. The "1" values for the zone under the negative control samples were likely due to physical mechanisms due to the high absorbency of the material. The qualitative, microscopically obtained data presented above was supplemented by the use of a commercially available assay system for detecting cytotoxicity and cell proliferation (Promega Corporation, Madison Wis., CellTiter 96® Aqueous One Solution Cell Proliferation Assay, G3580). Quantitative cell viability is measured via MTS tetrazolium reduction measured by formazan production. The results are normalized to blank controls with a non-compromised monolayer. LC(50) columns indicate the critical value showing a concentration of 50% cell death. For this particular test, if the average normalized absolute values of the cells are above the LC(50), it is considered passing. The results are presented below in Table 8.

TABLE 8

Average Normalized Absolute Values of Cells

| Sample | Reading* | SD | Normalized | Score |
|---|---|---|---|---|
| Blank | 2.188 | 0.265 | 1.00 | Pass |
| CC (EtO) | 1.607 | 1.305 | 0.734 | Pass |
| CC (no EtO) | 1.302 | 0.143 | 0.595 | Pass |
| FH | 1.763 | 0.046 | 0.806 | Pass |
| FM | 1.222 | 0.083 | 0.559 | Pass |
| (−) control | 1.350 | 0.116 | 0.617 | Pass |
| (+) control | 0.425 | 0.043 | 0.194 | Fail |

*Average of eight replicates

3. Contact Test Summary:

Refer to Table 9 below for the results of the contact test for sample CC. Note that (+) indicates growth on contact layer of material while (−) indicates no growth on contact layer of material. These results demonstrate biocompatibility, and that the materials treated with PEC will have no adverse effect on the body, as evidenced by the fact that no antimicrobial is transferred to the tissue that is in contact with the treated substrate.

TABLE 9

Contact Test Results for Sample CC after EtO Sterilization:

| Organism | ATCC ID# | Growth on Contact Layer |
|---|---|---|
| Staphylococcus aureus | ATCC 6538 | + |
| MRSA (Methicillin resistant S. aureus) | ATCC BAA-44 | + |
| Staphylococcus epidermis | ATCC 12228 | + |
| Pseudomonas aeruginosa | ATCC 15442 | + |
| Enterococcus faecalis | ATCC 19433 (10741) | + |
| VRE (Vancomycin resistant E. faecium) | ATCC 700221 | + |
| Escherichia coli | ATCC 15597 | + |
| Proteus mirabilis | ATCC 51393 (7002) | + |
| Klebsiella pneumoniae | ATCC 13883 | + |
| Streptococcus bovis | ATCC 43143 | + |
| Streptococcus pyogenes | ATCC 12344 (10096) | + |
| Serratia marcescens | ATCC 13880 | + |

Example 4

Treatment of Wood Pulp with PEC of polyDADMAC and Poly(Acrylic Acid)-Sodium Salt A stable dispersion of PEC in an aqueous carrier was prepared as described for the treatment solution given in Example 2. To 1.5 liters of this solution was added 50 g of wood pulp. The mixture was stirred for ten minutes, and then poured into a cheese press. The excess liquid was pressed from the pulp. The final weight of the damp pulp was 118.6 grams (137% wet pickup). The pulp was spread on a screen and dried in an oven at 80° C. for 18 hours. The resulting antimicrobial wood pulp is useful as a component of diapers, sanitary napkins, wound dressings, and in other applications where an absorbent antimicrobial material is desirable.

Example 5

Treatment of Microcrystalline Cellulose Powder with PEC of polyDADMAC and Poly(Acrylic Acid)-Sodium Salt A stable dispersion of PEC in an aqueous carrier was prepared as described for the treatment solution given in Example 2. To 0.5 liters of this solution was added 25 g of microcrystalline cellulose powder (Avicel PH-101 cellulose gel, 50 micron average particle size). The mixture was stirred for ten minutes, and then suction filtered through filter paper in a Buchner funnel. The resulting cake of damp material (48.5 g) was collected and coarsely ground prior to drying in an oven at 80° C. for 18 hours. The resulting antimicrobial cellulose powder is useful as a component of diapers, sanitary napkins, wound dressings, and in other applications where an absorbent antimicrobial material is desirable.

Example 6

Pilot Scale Treatment of a Rayon Substrate (240 gsm) with PEC of polyDADMAC and Poly(Acrylic Acid)-Sodium Salt A pilot scale run was made using the following materials and parameters:
Recipe for Treatment Liquid (in Weight %):
PD (Floquat FL 4540; 40% solids): 0.625%
PAA3 (Flosperse 10,000; 30% solids): 0.307%
3 M KOH (13.1% solids): 0.0205%
Deionized Water 99.05%
Observations:
pH-Value [9.3]
Prepared Quantity [100 kg]
Stable dispersion with milky appearance
Operational Parameters:
Substrate: 240 gsm (see description above)
Foulard Mechanically adaptable pair of rollers.
Oven Belt dryer without edge fixation of the web.
Width Before Coating [550 mm]
Width After Coating [540 mm]
Coated Length [140 m]
Target Wet Add-On [125%]
Target Dry Add-On Weight [1.04 g/m$^2$]
Wet Add-On Beginning [125.3%]
Wet Add-On End [122.0%]
Test Results:
Weight 253.7 g/m$^2$ (252.5 untreated)
Thickness 2.18mm (2.00 mm untreated)
Water Absorption 2185 g/m$^2$ (2389 untreated)
Antimicrobial Performance:

Treated substrate was tested according to methods described herein. Treated substrate was retested after treatment by EtO according to methods described herein.

| Bacterial Species | Log Reduction |
|---|---|
| PA | 6.4 Log (prior to EtO treatment) |
| PA | 7.4 Log (after EtO treatment) |
| EC | >6.0 Log ("full kill" both before and after EtO treatment) |
| SA | >6.0 Log ("full kill" both before and after EtO treatment) |

The data clearly shows that EtO treatment has a significant positive effect on antimicrobial efficacy.

Extract testing was performed on the treated substrates according to Extraction Method for Leachability Testing (QMT Method EX-1), described herein. The average level of PD in the extract of an as-prepared sample was found to be 41 (+/−10 ppm), and the average level of PD in the extract of a sample subjected to EtO treatment, as described herein, was found to be 57 (+/−1 ppm). In general, PD levels of less than approximately 60 ppm do not contribute to cytotoxicity, and have "no effect on the body".

Example 7

Pilot Scale Treatment of a Rayon Substrate (240 gsm) with PEC of polyDADMAC and Poly(Acrylic Acid)-Sodium Salt A pilot scale run was made using the following materials and parameters:
Recipe for Treatment Liquid (in Weight %):
PD (Floquat FL 4540; 40% solids): 0.625%
PAA3 (Flosperse 10,000; 30% solids): 0.307%
3 M KOH (13.1% solids): 0.0205%
Deionized Water 99.05%
Observations:
pH-Value [9.3]
Prepared Quantity [100 kg]
Stable dispersion with milky appearance
Operational Parameters:
Substrate: 115 gsm (see description above)
Foulard Mechanically adaptable pair of rollers.

Oven Belt dryer without edge fixation of the web.
Width Before Coating [550 mm]
Width After Coating [530 mm]
Coated Length [190 m]
Target Wet Add-On [125%]
Target Dry Add-On Weight [0.49 g/m$^2$]
Wet Add-On Beginning [125.4%]
Wet Add-On End [128.9%]
Test Results:
Weight 117.3 g/m$^2$ (115.0 untreated)
Thickness 1.05mm (1.11 mm untreated)
Water Absorption 774 g/m$^2$ (794 untreated)
Antimicrobial Performance:

Treated substrate was tested according to methods described herein. Treated substrate was retested after treatment by EtO according to methods described herein.

| Bacterial Species | Log Reduction |
|---|---|
| PA | 2.8 Log (prior to EtO treatment) |
| PA | 7.2 Log (after EtO treatment) |
| EC | >6.0 Log ("full kill" both before and after EtO treatment) |
| SA | >6.0 Log ("full kill" both before and after EtO treatment) |

The data clearly shows that EtO treatment has a significant positive effect on antimicrobial efficacy.

Extract testing was performed on the treated substrates according to Extraction Method for Leachability Testing (QMT Method EX-1), described herein. The average level of PD in the extract of an as-prepared sample was found to be 34 (+/−3 ppm), and the average level of PD in the extract of a sample subjected to EtO treatment, as described herein, was found to be 39 (+/−9 ppm). In general, PD levels of less than approximately 60 ppm do not contribute to cytotoxicity, and have "no effect on the body".

Example 8

Pilot Scale Treatment of a Cotton Gauze Substrate with PEC of polyDADMAC and Poly(Acrylic Acid)-Sodium Salt Materials for all tests were cotton gauze rolls imported from China, and cut from master roll size to size needed. Cationic and anionic polymers were PD and PAA3, respectively (as described herein). All mixing was performed in the pad bath, and substrate material was "14×6 weave" 100% cotton gauze that had been folded over in a tenter frame to give 2-ply material. Width of the 2 ply material used in the run was approximately 9". Approximately 3,000 to 10,000 linear yards of gauze was processed during each run. The pad bath was a 50 gallon tank with heating strips inside. This bath had ballast placed into it to permit a working volume of 15 gallons to be used. Mixing was performed either directly in the pad bath, or in a separate mix tank. Equipment was setup to give 120% wet pickup, and the concentrations of PD and PAA3 in the treatment liquid were adjusted to give the final on-fabric polymer contents described in the Table 10. Thus, the levels of each polymer in the treatment liquid are approximately 20% lower than the final dry on-fabric weights. Treatment liquids were prepared by adding pre-diluted ingredients followed by pH adjustment to pH 10.5 (±0.5) using sodium hydroxide.

Cotton gauze was routed to pass from the master roll, through the folding (tenter) frame, and into the pad bath. After passing through the solution-filled pad bath, the gauze passed between nip rolls to achieve a reproducible liquid content of 120% relative to its dry weight. After the nip rolls the gauze was passed through a 'rimpler', essentially a rotating roll that had a doctor blade moving back and forth across it. This produced crimped fabric that is folded regularly to provide stretch.

After the rimpler, the gauze fell onto a conveyor belt that carried it through a drier. The dryer passed the fabric through in a Z shape, passing the length of the dryer three times before exiting, with each successive pass (the gauze drops down to a conveyor belt below after each pass, with each successive stage moving slightly faster than the one above to stretch clumps of gauze out for better drying. Adhesion of the gauze to the bottom of the conveyor belt was resolved by installation of a pneumatic device to help the gauze detach from the conveyor. An infrared heating unit was installed at the exit of the dryer, which effectively removed any residual dampness from the gauze.

Treated cotton gauze substrate was subjected to treatment with EtO using methods described herein.

TABLE 10

Batch chemistries

| Sample ID | PD % | PAAS % | Mix volume (gallons) |
|---|---|---|---|
| 011909-01 | 0.300% | 0.096% | 20 |
| 011909-02 | 0.300% | 0.096% | 20 |
| 012009-03 | 0.300% | 0.096% | 20 |
| 012109-10 | 0.300% | 0.096% | 100 |

Antimicrobial efficacy was tested using methods described herein. Results are presented in Tables 11 and 12. The data in Table 12 demonstrates that EtO treatment has a significant positive effect on antimicrobial efficacy.

TABLE 11

Antimicrobial efficacy of treated cotton gauze substrate.

| Sample ID | Avg. Log Reduction (*Escherichia coliform*) | Avg. Reduction (*S. aureus*) | Avg. Log Reduction (*P. aeruginosa*) |
|---|---|---|---|
| 011909-01 | 6.9* | 5.7* | 3.6 |
| 011909-02 | 6.9* | 5.7* | 5.5 |
| 012009-03 | 7.5 | 6.7* | 6.9 |
| 012109-10 | 8.0* | 6.0* | 4.8 |

(*= full kill)

TABLE 12

Effect of EtO treatment on antimicrobial efficacy.

| Sample ID | Avg. Log Reduction (*P. aeruginosa*) No EtO treatment | Avg. Log Reduction (*P. aeruginosa*) with EtO treatment | Effect of EtO treatment on efficacy (Log Kill) |
|---|---|---|---|
| 011909-01 | 2.1 | 3.6 | +1.5 Log |
| 011909-02 | 3.8 | 5.5 | +1.7 Log |
| 012009-03 | 3.5 | 6.9 | +3.4 Log |
| 012109-10 | 5.2 | 4.8 | −0.4 Log |

Extract testing was performed on the treated substrates according to "Extraction Method for Leachability Testing" (QMT Method EX-1), described herein. Multiple sets of extraction tests (each with n=6) were performed on each batch. Results are presented in Table 13. The average content of PD in an extract of the treated substrate (after EtO treatment) was found to be 44 ppm. In general, PD levels of less than approximately 60 ppm do not contribute to cytotoxicity, and have "no effect on the body".

TABLE 13

Average values of PD concentration in different sets of extracts (in ppm).

| Sample ID | Set 1 (n = 6) [PD] in ppm | Set 2 (n = 6) [PD] in ppm | Set 3 (n = 6) [PD] in ppm | Set 4 (n = 6) [PD] in ppm | Average (all sets) [PD] in ppm |
|---|---|---|---|---|---|
| 011909-01 | 26 | 32 | 35 | | 31 |
| 011909-02 | 37 | 52 | 55 | | 48 |
| 012009-03 | 44 | 57 | 58 | | 53 |
| 012109-10 | | | | 47 | 47 |
| Overall average for ppm of polyDADMAC in extract (n = 60): | | | | | 44 |

Samples of the treated cotton gauze substrate materials prepared according to the described process were tested for cytotoxicity per ISO 10993-5 method. This method is comparable to ASTM F813-07 "*Standard Practice for Direct Contact Cell Culture Evaluation of Materials for Medical Devices*". There was no biological reactivity found for the samples tested (all testing was in triplicate). All wells evaluated showed a grade of 0 (grade 2 or lower is considered passing for this method). The observed cellular response from the positive control article (grades 3 and 4 at 24 h and 48 h respectively) and the negative control article (grade 0) confirm the proper functioning of the test system. The test articles (treated substrates) are therefore considered non-cytotoxic per this evaluation.

Sample of treated cotton gauze material were tested for primary skin irritation by a commercial testing laboratory. It was determined that the material was "non-irritating".

The invention claimed is:

1. A method of preparing an antimicrobial article which comprises the steps of
    a. providing a treatment liquid consisting essentially of a stable aqueous solution, colloid, suspension, dispersion, coacervate, or emulsion of a polyelectrolyte complex, PEC, prepared by mixing an aqueous solution of an anionic polyelectrolyte consisting essentially of a derivative or copolymer of poly(acrylic acid) or polystyrene sulfonate producing a concentration of 0.025 to 0.20 weight percent in said treatment liquid, with a stoichiometric excess of an aqueous solution of an antimicrobial cationic polyelectrolyte consisting essentially of a quaternary ammonium polymer or a quaternary ammonium copolymer producing a concentration of 0.10 to 0.50 weight percent in said treatment liquid, wherein the molar ratio of charge sites in said antimicrobial cationic polyelectrolyte relative to charge sites in said anionic polyelectrolyte is between 1:1 and 2:1, and wherein said anionic polyelectrolyte and said antimicrobial cationic polyelectrolyte have been mixed in a controlled manner to produce said PEC which remains evenly dispersed in said treatment liquid, and wherein there is no significant or non-reversible phase separation, coagulation, or formation of solids, precipitates, flocs, agglomerates, or particles of said PEC during the normal storage or usage of the treatment liquid,
    b. applying said treatment liquid to an article, followed by,
    c. drying the treated article, whereby PEC is non-leachably bound to the resulting antimicrobial article.

2. The method of claim 1, further comprising the step of rinsing the antimicrobial article after the drying step.

3. The method of claim 1, further comprising the step of treating the antimicrobial article with ethylene oxide, whereby the antimicrobial efficacy of the antimicrobial article is increased.

4. The method of claim 1, further comprising the steps of testing to verify that the antimicrobial article has non-leaching antimicrobial properties.

5. The method of claim 4, wherein said testing is selected from the group consisting of microbiological assays, in-vivo assays, in-vitro assays, dye tests, spectroscopy, colorimetry, and measurement of surface charge.

6. The method of claim 1, further comprising the step of testing to verify that the antimicrobial article is biocompatible.

7. The method of claim 6, wherein said testing is selected from the group consisting of cytotoxicity, irritation, and sensitization tests.

8. The method of claim 1, wherein the average molecular weight of said anionic polyelectrolyte is within the range of 20,000 and 75,000, and wherein the average molecular weight of said antimicrobial cationic polyelectrolyte is at least 50,000.

9. The method of claim 1, wherein the average molecular weight of said anionic polyelectrolyte is within the range of 20,000 and 75,000, and wherein the average molecular weight of said antimicrobial cationic polyelectrolyte is more than 200,000.

10. The method of claim 1, wherein the concentration of said antimicrobial cationic polyelectrolyte in said treatment liquid is between 0.20 and 0.30 weight percent.

11. The method of claim 1, wherein the concentration of said anionic polyelectrolyte is between 0.07 weight percent and 0.14 weight percent.

12. The method of claim 1, wherein a minimum of 3-log average reduction of the population of viable *Staphylococcus aureus* in the presence of 10% fetal bovine serum is obtained, when said antimicrobial article is tested using ATCC Method 100.

13. The method of claim 1, wherein an extract derived from the antimicrobial article prepared according to ISO standard method 10993-12 contains less than 100 ppm of said antimicrobial cationic polyelectrolyte.

14. The method of claim 1, wherein the molar ratio of charge sites in the antimicrobial cationic polyelectrolyte and the charge sites in the anionic polyelectrolyte is within the range of 1.3:1 and 2:1.

15. The method of claim 1, wherein the antimicrobial cationic polyelectrolyte is poly(diallyldimethylammonium chloride), also known as polyDADMAC, and the anionic polyelectrolyte is a sodium, potassium, lithium, or ammonium salt of poly(acrylic acid).

16. The method of claim 1, wherein the antimicrobial cationic polyelectrolyte is polyDADMAC, the anionic polyelectrolyte is the sodium salt of poly(acrylic acid), and the antimicrobial article comprises cotton or rayon.

17. An antimicrobial article, comprising an article, an antimicrobial cationic polyelectrolyte, and an anionic polyelectrolyte, prepared by the process of claim 1.

18. The antimicrobial article of claim 17, wherein said antimicrobial article is comprised of materials selected from the group consisting of cellulose, cellulose derivatives, paper, wood, wood pulp, microbially-derived cellulose, microcrystalline cellulose, hydroxyethyl cellulose, carboxymethyl cellulose, methyl cellulose, rayon, cotton, wood pulp, linen, polysaccharide, protein, wool, collagen, gelatin, chitin, chitosan, alginate, starch, silk, polyolefin, polyamide, fluoropolymer, polyvinyl chloride, vinyl, rubber, polylactide, polyglycolide, acrylic, polystyrene, polyethylene, polypropylene, nylon, polyester, polyurethane, and silicone.

19. The antimicrobial article of claim 17, wherein said antimicrobial cationic polyelectrolyte is poly(diallyldimethylammonium) chloride, also known as polyDADMAC.

20. The antimicrobial article of claim 17, wherein the anionic polyelectrolyte is selected from the group consisting of sodium, potassium, lithium, or ammonium salts of poly(acrylic acid) and its derivatives or copolymers.

21. The antimicrobial article of claim 17, wherein the antimicrobial cationic polyelectrolyte is polyDADMAC, and the anionic polyelectrolyte is the sodium salt of poly(acrylic acid).

22. The antimicrobial article of claim 21, wherein said antimicrobial article further comprises cotton or rayon.

23. The antimicrobial article of claim 17, comprising an article, an antimicrobial cationic polyelectrolyte, and an anionic polyelectrolyte, wherein the molar ratio of charge sites in the antimicrobial cationic polyelectrolyte to the charge sites in the anionic polyelectrolyte is between 1.3:1 and 2:1.

24. The antimicrobial article of claim 17, wherein the average degree of polymerization of said antimicrobial cationic polyelectrolyte is in the range of about 10 to 10,000.

25. The antimicrobial article of claim 17, wherein the average degree of polymerization of said antimicrobial cationic polyelectrolyte is in the range of about 100 to 5,000.

26. The antimicrobial article of claim 17, wherein the concentration of antimicrobial cationic polyelectrolyte in said antimicrobial article is between 0.01 w/o and 1.0 weight percent.

27. The antimicrobial article of claim 18, wherein said antimicrobial article is a wound dressing, medical device, or clothing.

28. The antimicrobial article of claim 17, wherein said antimicrobial article is further treated with ethylene oxide, whereby the antimicrobial efficacy of said antimicrobial article is increased.

29. A method of preparing a treatment liquid which comprises the step of
   a. mixing, in a controlled manner, an aqueous solution of an anionic polyelectrolyte consisting essentially of a derivative or copolymer of poly(acrylic acid) or polystyrene sulfonate having a concentration of 0.025 to 0.20 weight percent in the treatment liquid, and a stoichiometric excess of an aqueous solution of an antimicrobial cationic polyelectrolyte consisting essentially of a quaternary ammonium polymer or a quaternary ammonium copolymer having a concentration of 0.10 to 0.5 weight percent in the treatment liquid, wherein the molar ratio of charge sites in said antimicrobial cationic polyelectrolyte relative to charge sites in said anionic polyelectrolyte is between 1:1 and 2:1, to produce a treatment liquid consisting essentially of a stable aqueous solution, colloid, suspension, dispersion, coacervate, or emulsion of a polyelectrolyte complex, PEC which remains evenly dispersed in said treatment liquid, and wherein there is no significant or non-reversible phase separation, coagulation, or formation of solids, precipitates, flocs, agglomerates, or particles of said PEC during the normal storage usage of the treatment liquid.

30. The method of claim 29, wherein the molar ratio of charge sites in said antimicrobial cationic polyelectrolyte relative to the charge sites in said anionic polyelectrolyte is between 1.3:1 and 2:1.

31. The method of claim 29, wherein the concentration of said antimicrobial cationic polyelectrolyte in said treatment liquid is between 0.20 and 0.30 weight percent.

32. The method of claim 29, wherein the concentration of said anionic polyelectrolyte is between 0.07 and 0.14 weight percent.

33. The method of claim 29, wherein said mixing in is by stirring, shaking, homogenization, blending, sonication or high-shear mixing.

34. The method of claim 29, wherein said treatment liquid has a pH between 8 and 10.

35. A treatment liquid made by the process of claim 29.

36. The treatment liquid of claim 35, wherein the ratio of charge sites in said antimicrobial cationic polyelectrolyte to the charge sites in said anionic polyelectrolyte is within the range of 1.3:1 and 2:1.

37. The treatment liquid of claim 35, wherein the average molecular weight of said anionic polyelectrolyte is within the range of 20,000 and 75,000, wherein the average molecular weight of said antimicrobial cationic polyelectrolyte is at least 50,000.

38. The treatment liquid of claim 35, wherein the average molecular weight of said anionic polyelectrolyte is within the range of 20,000 and 75,000, wherein the average molecular weight of said antimicrobial cationic polyelectrolyte is at more than 200,000.

39. The treatment liquid of claim 35, wherein the concentration of said antimicrobial cationic polyelectrolyte in said treatment liquid is between 0.20 and 0.30 weight percent.

40. The treatment liquid of claim 35, wherein the concentration of said anionic polyelectrolyte is between 0.07 and 0.14 weight percent.

41. The treatment liquid of claim 35, wherein the pH of said treatment liquid is between 8 and 10.

* * * * *